US008470855B2

(12) United States Patent
Ansorge et al.

(10) Patent No.: US 8,470,855 B2
(45) Date of Patent: Jun. 25, 2013

(54) DUAL-USE PEPTIDASE INHIBITORS AS PRODRUGS FOR A THERAPY OF INFLAMMATORY AND OTHER DISEASES

(75) Inventors: Siegfried Ansorge, Hohenwarthe (DE); Klaus Neubert, Halle (DE); Ute Bank, Stassfurt (DE); Irene Reichstein, Halle (DE); Jürgen Faust, Halle (DE); Michael Täger, Heinrichsberg (DE); Petra Fuchs, Halle (DE); Bianca Senns, Halle (DE)

(73) Assignee: IMTM GmbH, Magdeburg (DE)

( * ) Notice: Subject to any disclaimer, the term of this patent is extended or adjusted under 35 U.S.C. 154(b) by 624 days.

(21) Appl. No.: 12/085,096

(22) PCT Filed: Nov. 10, 2006

(86) PCT No.: PCT/EP2006/010818
§ 371 (c)(1),
(2), (4) Date: Aug. 14, 2008

(87) PCT Pub. No.: WO2007/057128
PCT Pub. Date: May 24, 2007

(65) Prior Publication Data
US 2009/0124667 A1 May 14, 2009

(30) Foreign Application Priority Data

Nov. 16, 2005 (DE) .......................... 10 2005 054 700

(51) Int. Cl.
| | | |
|---|---|---|
| *A61K 31/4439* | (2006.01) | |
| *A61K 31/444* | (2006.01) | |
| *A61K 31/427* | (2006.01) | |
| *A61K 31/4025* | (2006.01) | |
| *C07D 277/04* | (2006.01) | |
| *C07D 207/04* | (2006.01) | |
| *C07D 401/02* | (2006.01) | |
| *C07D 401/14* | (2006.01) | |
| *C07D 417/02* | (2006.01) | |
| *C07D 417/14* | (2006.01) | |

(52) U.S. Cl.
USPC ........... 514/340; 514/342; 514/343; 514/365; 514/422; 514/423; 546/269.7; 546/256; 546/279.1; 548/200; 548/518; 548/523; 548/540

(58) Field of Classification Search
USPC .. 514/365, 423, 340, 342, 343, 422; 548/200, 548/540, 523, 518; 546/269.7, 256, 279.1
See application file for complete search history.

(56) References Cited

U.S. PATENT DOCUMENTS 5,939,560 A 8/1999 Jenkins et al.

FOREIGN PATENT DOCUMENTS

| | | |
|---|---|---|
| DE | 101 02 392 | 8/2002 |
| DE | 103 30 842 | 2/2005 |
| DE | 103 37 074 | 3/2005 |
| WO | WO 01/89569 | 11/2001 |
| WO | WO 02/053169 | 7/2002 |
| WO | WO 02/053170 | 7/2002 |
| WO | WO 2005/034940 | 4/2005 |

OTHER PUBLICATIONS

Schafer et al. Drug Discovery Today 2008, 13 (21/22), 913-916.*

(Continued)

*Primary Examiner* — Jason M Nolan
(74) *Attorney, Agent, or Firm* — D. Peter Hochberg; Sean F. Mellino

(57) ABSTRACT

Compounds of the general formulae (1) and (2)

A-B-D-B'-A'    (1)

and

A-B-D-E    (2)

in which
A and A' may be identical or different and are the residue

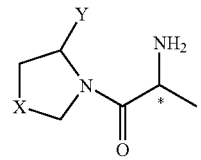

in which X is S, O, $CH_2$, $CH_2CH_2$, $CH_2O$ or $CH_2NH$, and Y is H or CN, and * designates a chiral carbon atom preferably in S- or L-configuration;

B and B' may be identical or different and are an O, N or S containing or non-containing, unsubstituted or substituted, unbranched or branched alkylene residue, cycloalkylene residue, aralkylene residue, heterocycloalkylene residue, heteroarylalkylene residue, arylamidoalkylene residue, heteroarylamidoalkylene residue, unsubstituted or mono- or poly-substituted arylene residue or heteroarylene residue having one or more five-, six- or seven-membered ring(s);

D is —S—S— or —Se—Se—; and

E is the group —$CH_2$—$CH(NH_2)$—$R^9$ or —$CH_2$—*$CH(NH_2)$—$R^9$ respectively in which $R^9$ is an O, N or S containing or non-containing, unsubstituted or substituted, unbranched or branched alkyl residue, cycloalkyl residue, aralkyl residue, heterocycloalkyl residue, heteroarylalkyl residue, arylamidoalkyl residue, heteroarylamidoalkyl residue, unsubstituted or mono- or poly-substituted aryl residue or heteroaryl residue having one or more five-, six- or seven-membered ring(s) and * designates a chiral carbon atom preferably in the S- or L-configuration;

or the acid addition salts thereof with organic and/or inorganic acids; as well as to the use of the compounds of the general formulae (1) and (2) in medicine.

29 Claims, 4 Drawing Sheets

OTHER PUBLICATIONS

Horig et al. Journal of Translational Medicine 2004, 2(44).*
P. Kirkpatrick, Nature Reviews Drug Discovery 2002, 1, 486-487.*
J.R. White, Clinical Diabetes 2008, 26(2), 53-57.*
ClinicalTrials.gov (Oct. 2011): http://www.clinicaltrials.gov/ct2/show/NCT00824980+48 term=aminopeptidase+N&rank=1.*
Shimazawa, R., et al.; "Novel Small Molecule Nonpeptide Aminopeptidase N Inhibitors with a Cyclic Imide Skeleton;" *Journal of Enzyme Inhibition*; vol. 14, No. 9 (1999); pp. 259-275.
T. Chen et al.: Adv. Exp. Med. Biol. 524, 79, 2003.
J. S. Duke-Cohan et al.: J. Immunol. 156, 1714, 1996.
A. J. Barrett et al.: Handbook of Proteo-lytic Enzymes, Academic Press 1998.
M. Komodo et al.: Bioorg. and Med. Chem. 9, 121, 2001.
U. Lendeckel et al.: Intern. J. Mol. Med. 4, 17, 1999.
T. Kähne et al.: Intern. J. Mol. Med. 4, 3, 1999.
I. De Meester et al.: Advanc. Exp. Med. Biol. 524, 3, 2002.
D. P. Kontoyiannis et al.: Lancet 361, 1558, 2003.
D. M. Evans: Drugs 5, 577, 2002.
M.-C. Fournie-Zaluski and B. P. Rogues: in J. Langner and S. Ansorge: Ectopeptidases, Kluwer Academic/Plenum Publishers, p. 51, 2002.
Barrett, A.J., et al.; *Handbook of Proteo-lytic Enzymes*; Academic Press (1998).
Chen, T., et al.; "Dipeptidyl Peptidase IV Gene Family;" *Adv. Exp. Med. Biol.*; vol. 524, pp. 79-86 (2003).
De Meester, Ingrid, et al.; "Dipeptidyl Peptidase IV Substrates;" *Advanc. Exp. Med. Biol.*; 524, p. 3-17 (2002).
Duke-Cohan, J.S., et al.; "Serum High Molecular Weight Dipeptidyl Peptidase IV (CD26) is Similar to a Novel Antigen DPPT-L Released from Activated T Cells;" *J. Immunol.*; vol. 156, pp. 1714-1721 (1996).
Evans, D. Michael; "Dipeptidyl Peptidase IV Inhibitors;" *Drugs*; vol. 5, pp. 577-585 (2002).
Fournie-Zaluski, Marie-Claude and Rogues, Bernard P; "New Selective Aminopeptidase N Inhibitors as Potential Therapeutics;" *Ectopeptidases*; pp. 51-94 (2002).
Kähne, T., et al.; "Dipeptidyl Peptidase IV: A cell surface peptidase involved in regulating T cell growth (Review);" *Intern. J. Mol. Med.*; vol. 4, pp. 3-15 (1999).
Komodo, M., et al.; "Specific Inhibitor of Puromycin-Sensitive Aminopeptidase with a Homophthalimide Skeleton: Identification of the Target Molecule and a Structure-Activity Relationship Study;" *Bioorganic & Medicinal Chemistry*; vol. 9, pp. 121-131 (2001).
Kontoyiannis, D.P., et al.; "Aminopeptidase N Inhibitors and SARS;" *The Lancet*; vol. 361, p. 1558 (2003).
Lendeckel, Uwe, et al.; Role of Alanyl Aminopeptidase in Growth and Function of Human T cells (Review); *Intern. J. Mol. Med.*; vol. 4, pp. 17-27 (1999).
Ino, K. et al.; "Inhibitory effect of bestatin on the growth of human lymphocytes;" *Immunopharmacology*; vol. 23, p. 163-171 (1992).
Lendeckel, U. et al.; "Induction of the membrane alanyl aminopeptidase gene and surface expression in human T-cells by mitogenic activation,;" *Biochem. J.*; vol. 319, p. 817-821 (1996).
Nagai, M. et al.; "Phebestin a new inhibitor of Aminopeptidase N;" *The Journal of Antibiotics*; vol. 50, No. 1, p. 82-84 (1996).

* cited by examiner

Figure 1: Inhibition of the phytohaemagglutinine-induced proliferation of mononuclear cells (MNC) of healthy donors by examples for substances given in tables 3 and 4 (V – XIII).

Figure 2: Therapeutic effect of substance VII (given in table 4) in mouse model of colitis (DSS-colitis).

Figure 3: Therapeutic effect of substance VII (given in table 4) in mouse model of colitis (DSS-colitis).

Scheme of synthesis 1 for compounds A – B – D – B' – A' and A – B – D - E

DUAL-USE PEPTIDASE INHIBITORS AS PRODRUGS FOR A THERAPY OF INFLAMMATORY AND OTHER DISEASES

CROSS-REFERENCE TO RELATED APPLICATIONS

This application is a National Stage application of International Application No. PCT/EP2006/010818, filed on Nov. 10, 2006, which claims priority of German application number 10 2005 054 700.1, filed on Nov. 16, 2005, both of which are incorporated herein by reference in their entireties.

BACKGROUND OF THE INVENTION

1. Field of the Invention

The invention relates to novel substances and compounds which are capable of concertedly inhibiting the enzymes dipeptidyl peptidase IV (DPIV) as well as peptidases having an analogous enzymatic effect and alanyl aminopeptidase N (APN) as well as peptidases having an analogous enzymatic effect ("dual inhibitors"). Furthermore, the invention relates to processes to prepare the novel dual inhibitors of DPIV and APN. The invention also relates to the afore-mentioned novel compounds for a use in the medical field. Moreover, the invention relates to a use of the afore-mentioned dual inhibitors for a prophylaxis and a therapy of diseases showing an excessive immune response and having an inflammatory genesis, of neuronal diseases and of cerebral damage, of tumor diseases, of skin diseases, of diabetes of the type II and of SARS.

2. Description of the Prior Art

The enzyme dipeptidyl peptidase IV (DPIV, CD26, EC 3.4.14.5) is a serine protease existing ubiquituously and catalyzing the hydrolysis of peptides specifically after proline and—to a lesser extent—after alanine or—with restrictions—after further amino acids like serine, threonine, valine and glycine at the second position of the N-terminus. Enzymes belonging to the gene family of enzymes having DPIV-analogous enzymatic effect are—inter alia—DP 8, DP 9 and FAP/seprase [T. Chen et al.: Adv. Exp. Med. Biol. 524, 79, 2003]. A substrate specifity analogous to DPIV was also found for attractin (mahagony protein) [J. S. Duke-Cohan et al.: J. Immunol. 156, 1714, 1996]. Said enzyme is also inhibited by DPIV inhibitors.

Belonging to the group of alanyl aminopeptidases (also existing ubiquituously) are the aminopeptidase N (APN, CD13, EC 3.4.11.2) predominantly appearing as a membrane protein of the type II, as well as the cytosolic soluble alanyl aminopeptidase (EC 3.4.11.14, puromycine-sensitive aminopeptidase, amino-peptidase PS, encephaline-degrading aminopeptidase). Alanyl aminopeptidases (including the afore-mentioned aminopeptidases) act in dependency of a metal, for example in dependency of zinc, and catalyze the hydrolysis of peptide bonds after the N-terminal amino acids of oligopeptides, in the case of APN with a preference of alanine at the N-terminus [A. J. Barrett et al.: Handbook of Proteo-lytic Enzymes, Academic Press 1998]. All inhibitors of aminopeptidase N also inhibit the cytosolic alanyl aminopeptidase, while specific inhibitors of the cytosolic aminopeptidase exist [M. Komodo et al.: Bioorg. and Med. Chem. 9, 121, 2001].

For both groups of enzymes, important biologic functions were proved in different cell systems. This is true—inter alia—for the immune system [U. Lendeckel et al.: Intern. J. Mol. Med. 4, 17, 1999; T. Kähne et al.: Intern. J. Mol. Med. 4, 3, 1999; I. De Meester et al.: Advanc. Exp. Med. Biol. 524, 3, 2002; International Patent Application No. WO 01/89,569; International Patent Application No. WO 02/053,170; International Patent Application No. PCT/EP 03/07,199]; the neuronal system [International Patent Application No. WO 02/053,169 and German Patent Application No. 103 37 074.9]; the fibroblasts [German Patent Application No. 103 30 842.3]; the keratinocytes [International Patent Application No. WO 02/053,170]; the sebaceous gland cells/sebatocytes [International Patent Application No. PCT/EP 03/02,356]; tumors as well as for virus-caused infections as, for example coronavirusses [D. P. Kontoyiannis et al.: Lancet 361, 1558, 2003].

The capability, of DPIV, of specifically inactivating the incretory hormones GIP and GLP led to the development of a new therapeutic concept for treating glucose metabolic disorders [D. M. Evans: Drugs 5, 577, 2002].

For both groups of enzymes, there are known different inhibitors [reviews are found in: D. M. Evans: Drugs 5, 577, 2002; and: M.-C. Fournie-Zaluski and B. P. Roques: in J. Langner and S. Ansorge: Ectopeptidases, Kluwer Academic/Plenum Publishers, p. 51, 2002].

The isolated inhibition of the alanyl aminopeptidases and of the dipeptidyl peptidase IV as well as the inhibition of enzymes having an analogous substrate specificity, in particular the combined inhibition of enzymes of both groups of enzymes, results into a strong inhibition of the DNA synthesis of immune cells and, hence, into a strong inhibition of the cell propagation as well as into a change of the cytokine production, particularly into an induction of the (immune-regulatory effective) TGF-β1 [International Patent Application No. WO 01/89,569; International Patent Application No. WO 02/053, 170] as well as into an inhibition of the generation and release of inflammatory cytokines of the type TH1 and TH2, e.g. interleukine-4 (IL-4) [International Patent Application No. WO 02/053,170 and German Patent Application No. 101 02 392.8]. Inhibitors of alanyl aminopeptidase effect a strong induction of TGF-β1 at regulatory T-cells [International Patent Application No. PCT/EP 03/07,199]. In the neuronal system, a decrease or retardation of acute and chronic cerebral damage processes was proved by an inhibition of both enzyme systems [International Patent Application No. WO 02/053,169 and German Patent Application No. 103 37 074.9]. Moreover, it was proved for fibroblasts [German Patent Application No. 103 30 842.3], keratinocytes [International Patent Application No. WO 02/053,170) and sebatocytes [International Patent Application No. PCT/EP 03/02, 356] that the combined inhibition of alanyl aminopeptidase N and DPIV effects an inhibition of the growth and a change of the cytokine production.

This results into the surprising fact that the alanyl aminopeptidases and the dipeptidyl peptidase IV as well as enzymes having an analogous effect perform fundamental central biologic functions in different organs and cell systems, and that a combined inhibition of both groups of enzymes represents a new effective therapeutic principle for the treatment of various—im most cases chronic—diseases.

In accepted animal models, the applicants could show in the meantime that, in particular, the combined administration of inhibitors on both groups of said peptidases results into an inhibition of the growth of different cell systems and into a suppression of an excessive immune response, of chronic inflammatory processes and of cerebral damages, also in vivo [International Patent Application No. WO 01/89,569]. The isolated administration of single known inhibitors results into a diminished effect.

The results reported up to now were obtained predominantly by means of known inhibitors of alanyl aminopeptidase N and dipeptidyl peptidase IV alone, being described in the literature and being—in part—commercially available but in particular by combinations of inhibitors of enzymes of both groups.

SUMMARY OF THE PRESENT INVENTION

Now, surprisingly, novel, predominantly non-peptidic low molecular weight substances were found, which may be employed as prodrugs and which may react under physiological and pathological conditions to effective agents or to a mixture of effective agents and which inhibit alanyl aminopeptidase N and enzymes having an analogous substrate specificity, and dipeptidyl peptidase IV and enzymes having an analogous substrate specificity as well, in a dual manner. The conversion of the prodrugs is conducted by a reduction of —S—S— or —Se—Se— bridges, preferably by cellular thiols (compounds bearing —SH-groups).

Hence, prodrugs of the type disclosed here preferably act at cells and tissues. Moreover, by the use of said prodrugs, a reduction of the inhibitory capacity of the inhibitors by binding to free peptidases in the blood plasma can be prevented from occurring.

Hence, the invention relates to novel substances which are capable of specifically inhibiting peptidases cleaving Ala-p-nitroanilide as well as peptidases cleaving Gly-Pro-p-nitroanilide and, hence, combine the capability of a concerted inhibition of both groups of peptidases in one substance, only.

DETAILED DESCRIPTION OF THE PRESENT INVENTION

Figure 1:
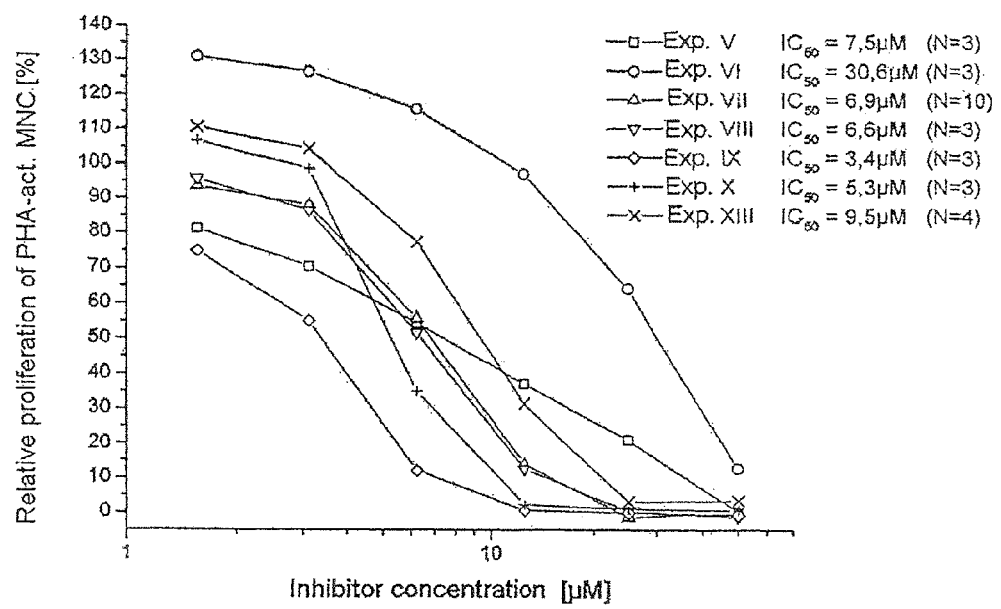
FIG. 1 is a graph showing the inhibitor concentration against the relative proliferation.

Moreover, the invention relates to novel substances which may be used as such, but also may be used as starting materials for other substances, for a prophylaxis and a therapy of diseases having an excessive immune response (autoimmune diseases, allergies and transplant rejections, sepsis), of other chronic-inflammatory diseases, including arteriosclerosis, neuronal diseases, and cerebral damage, skin diseases (inter alia acne and psoriasis), of tumor diseases and specific virus infections (inter alia SARS) as well as type II diabetes.

The invention relates to compounds of the general formulae (1) and (2)

A-B-D-B'-A'      (1) and

A-B-D-E      (2), in which

A and A' may be identical or different and are the residue

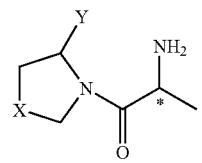

in which X is S, O, $CH_2$, $CH_2CH_2$, $CH_2O$ or $CH_2NH$, and Y is H or CN, and * designates a chiral carbon atom;

B and B' may be identical or different and are an O, N or S containing or non-containing, unsubstituted or substituted, unbranched or branched alkylene residue, cycloalkylene residue, aralkylene residue, heterocycloalkylene residue, heteroarylalkylene residue, arylamidoalkylene residue, heteroarylamidoalkylene residue, unsubstituted or mono- or poly-substituted arylene residue or heteroarylene residue having one or more five-, six- or seven-membered ring(s);

D is —S—S— or —Se—Se—; and

E is the group —$CH_2$—*$CH(NH_2)$—$R^9$ in which $R^9$ is an O, N or S containing or non-containing, unsubstituted or substituted, unbranched or branched alkyl residue, cycloalkyl residue, aralkyl residue, heterocycloalkyl residue, heteroarylalkyl residue, arylamidoalkyl residue, heteroarylamidoalkyl residue, unsubstituted or mono- or poly-substituted aryl residue or heteroaryl residue having one or more five-, six- or seven-membered ring(s) and * designates a chiral carbon atom;

or the acid addition salts thereof with organic and/or inorganic acids.

Preferred embodiments of the compounds of the general formulae (1) and (2) result from subclaims 2 to 10.

The invention also relates to a process to prepare compounds of the general formulae (1) and (2) according to the general scheme of synthesis given on the following page in which A, A', B, B', D and E have the meanings mentioned above in detail, in which according to the following scheme of synthesis 1

Scheme of synthesis 1 for compounds A-B-D-B'-A' and A-B-D-E

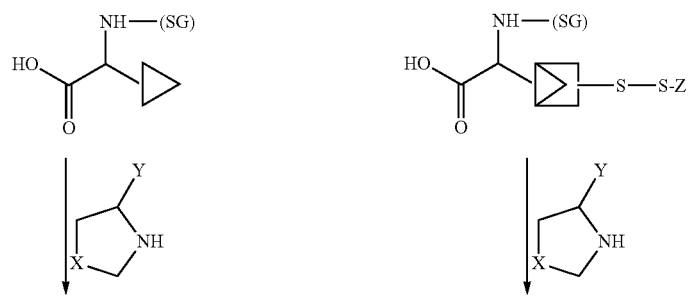

-continued

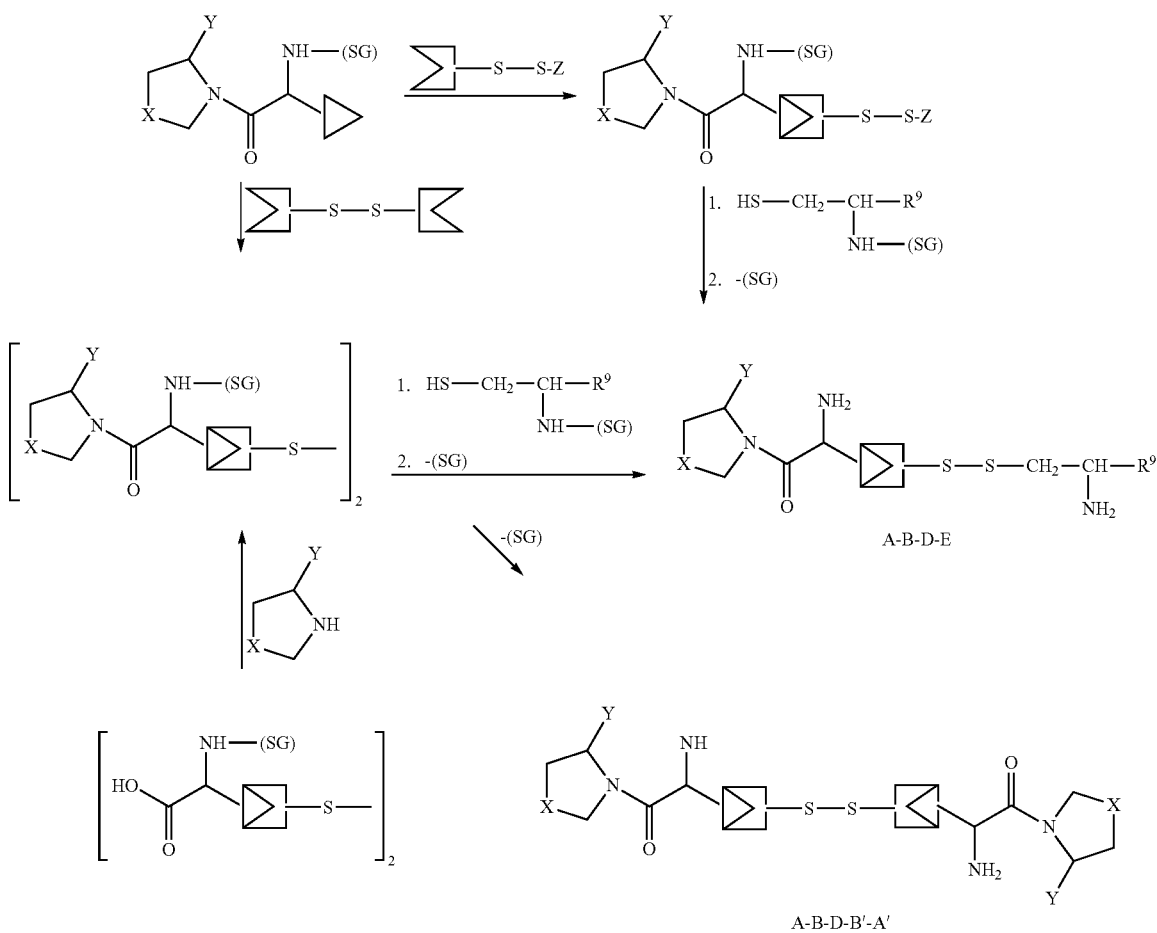

compounds of the general formula

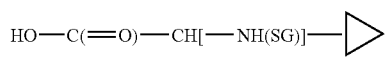

in which (SG) is a protecting group and

is a structure element of B are transformed with a heterocyclic compound of the general formula

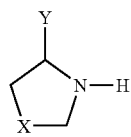

in which X is S, O, $CH_2$, $CH_2CH_2$, $CH_2O$ or $CH_2NH$ and Y is H or CN; the obtained condensation product of the formula

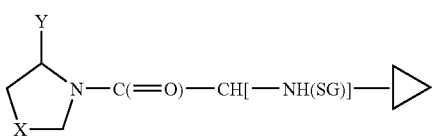

is transformed with a compound of the general formula

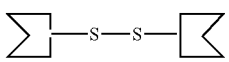

in which

is a structure element of B; and the resulting reaction product is transformed being cleaved from the protecting groups (SG) into a compound of the general formula A-B-D-B'-A' (1) in which A and A' may be identical or different and B and B' may be identical or different and in which A, A', B, B' and D may have the afore-mentioned meanings; or compounds of the general formula

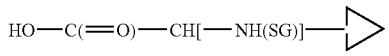

in which (SG) is a protecting group and

is a structure element of B are transformed with a heterocyclic compound of the general formula

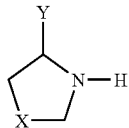

in which X is S, O, $CH_2$, $CH_2CH_2$, $CH_2O$ or $CH_2NH$ and Y is H or CN; the resulting condensation product of the formula

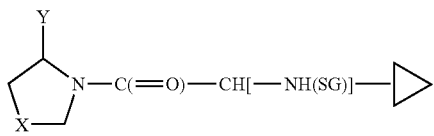

is transformed with a compound of the general formula

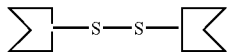

in which

is a structure element of B; and the resulting reaction product is transformed with a compound of the general formula $HS-CH_2-CH[-NH-(SG)]-(R^9)$ and is transformed being cleaved from the protecting groups (SG) into a compound of the general formula A-B-D-E (2), in which A, B, D and E may have the afore-mentioned meanings; or a compound of the general formula

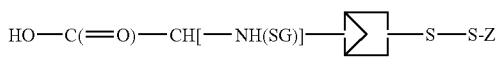

in which (SG) is a protecting group,

is a structure element of B and Z is a residue, which activates an —S—S-group for a thiol exchange, is transformed with a heterocyclic compound of the general formula

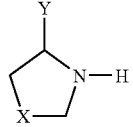

in which X is S, O, $CH_2$, $CH_2CH_2$, $CH_2O$ or $CH_2NH$ and Y is H or CN; the obtained condensation product of the formula

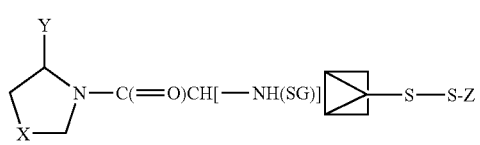

is transformed with a compound of the general formula $HS-CH_2-CH[-NH-(SG)]-(R^9)$ being cleaved from the protecting groups (SG) into a compound of the general formula A-B-D-E (2), in which A, B, D and E may have the afore-mentioned meanings; or a compound of the general formula

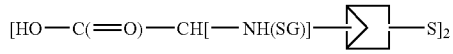

in which SG is a protecting group and

is a structure element of B is transformed with a heterocyclic compound of the general formula

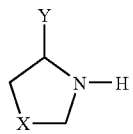

in which X is S, O, $CH_2$, $CH_2CH_2$, $CH_2O$ or $CH_2NH$ and Y is H or CN; and the obtained reaction product is transformed with a compound of the general formula $HS-CH_2-CH[-NH-(SG)]-R^9$ into a compound of the general formula A-B-D-E (2) in which A, B, D and E may have the afore-mentioned meanings; or a compound of the general formula

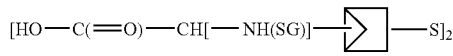

in which SG is a protecting group and

is a structure element of B, is transformed with a heterocyclic compound of the general formula

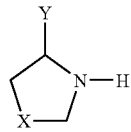

in which X is S, O, $CH_2$, $CH_2CH_2$, $CH_2O$ or $CH_2NH$ and Y is H or CN; and the obtained reaction product is transformed being cleaved from the protecting groups into a compound of the general formula A-B-D-B'-A' (1) in which A and A' may be identical or different and B and B' may be identical or different and in which A, A', B, B' and D may have the afore-mentioned meanings or compounds of the general formula

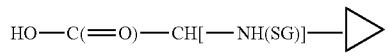

in which (SG) is a protecting group and

is a structure element/of B are transformed with a heterocyclic compound of the general formula

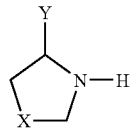

in which X is S, O, $CH_2$, $CH_2CH_2$, $CH_2O$ or $CH_2NH$ and Y is H or CN; the obtained condensation product of the formula

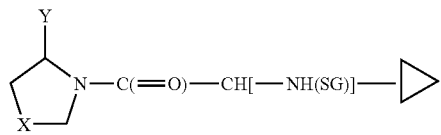

is transformed with a compound of the general formula

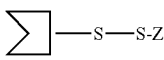

in which

is a structure element of B and Z is a residue which activates an —S—S-group for a thiol exchange and (SG) is a protecting group; and the obtained reaction product of the formula

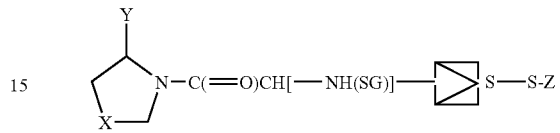

is transformed with a compound of the general formula

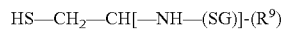

being cleaved from the protecting group (SG) into a compound of the general formula A-B-D-E (2) in which A, B, D and E may have the afore-mentioned meanings.

The invention also relates to the afore-mentioned and in the following in detail described compounds of the general formulae (1) and (2) to be used in medicine.

Furthermore the invention relates to the afore-mentioned and in the following in detail described compounds of the general formulae (1) and (2) being inhibitor precursors or inhibitor prodrugs.

Preferred embodiments result from subclaims 14 to 16.

Furthermore, the invention relates to the use of at least one compound of the afore-mentioned and in the following in more detail described general formulae (1) and (2) for the prophylaxis and therapy of diseases with exceeding immune response and inflammatory genesis including arteriosclerosis, neuronal diseases, cerebral damages, skin diseases, tumour diseases and virus-caused diseases, as well as type II diabetes.

The invention also relates to the use of at least one of the compounds of the afore-mentioned and in the following in detail described general formulae (1) and (2) for the preparation of a medicament for the prophylaxis and therapy of diseases with exceeding immune response and inflammatory genesis including arteriosclerosis, neuronal disease, cerebral damages, skin diseases, tumour diseases and virus-caused diseases, as well as type II diabetes.

Preferred embodiments of the use are claimed in claims 19 to 20.

Furthermore, the invention relates to a process to generate at least one inhibitor of dipeptidyl peptidase IV (DPIV) and of peptidases with analogous enzymatic effect, as well as of analyl aminopeptidase N (APN) and of peptidases with analogous enzymatic effect from at least one of the compounds of general formulae (1) and (2) according to the following detailed description, wherein at least one compound of the general formulae (1) and (2) is according to the following detailed description exposed to reducing conditions as they are present in cells and tissues.

Preferred embodiments of the process result from claim 22.

The invention relates also to pharmaceutical or cosmetic preparations comprising at least one of the compounds of at least one of the general formulae (1) and (2) according to one of the claims 1 to 10 and according to the following detailed description, optionally in combination with one or more pharmaceutical or cosmetic acceptable carrier(s), auxiliary compound(s) and/or adjuvant(s).

According to the invention the new compounds have either the general formula (1):

A-B-D-B'-A'     (1)

or the general formula (2):

A-B-D-E     (2),

It was surprisingly found that the compounds of said formulae themselves have inhibitory effects with regard to the enzymes mentioned below and moreover react to compounds under defined conditions which are inhibitors of dipeptidyl peptidase IV (DPIV) and of peptidases with analogous enzymatic effect, the analyl aminopeptidase N (APN) and of peptidases with analogous enzymatic effect.

Using the term "dipeptidyl peptidase IV" (DPIV, CD26, EC 3.4.14.5) in the following description and in the claims, the serine protease is recognized which catalyzes the hydrolysis of peptide bonds specifically after proline and to a lesser degree alanine and—with restrictions—after other amino acids like serine, threonine, valine, and glycine respectively at the second position of the N-terminus of peptides.

Using the term "peptidases with dipeptidyl peptidase IV analogous enzymatic effect" peptidases are recognized in the present description and in the claims which catalyze the hydrolysis of peptides specifically after proline or alanine at the second position of the N-terminus. Examples for peptidases with dipeptidyl peptidase IV analogous enzymatic effect are, without restricting the invention to those, DP 8, DP 9 and FAP/seprase [T. Chen et al., a. a. O.] and attractin (mahagony protein) [J. S. Duke-Cohan et al., a. a. O.].

Using the term "alanyl aminopeptidase N" (APN, CD13, EC 3.4.11.2) in the present description and in the claims the protease is recognized which operates metal-(zinc-) dependent and catalyzes the hydrolysis of peptide bonds specifically after N-terminal amino acids of peptides and preferably alanine at the N-terminus.

Using the term "peptidases with alanyl aminopeptidase N analogous enzymatic effect" peptidases are recognized in the present description and in the claims which—like APN—operate metal-dependent and catalyze the hydrolysis of peptide bonds specifically after N-terminal amino acids of peptides and preferably after alanine at the N-terminus. An example of a peptidase with alanyl aminopeptidase N analogous enzymatic effect is, without restricting the invention thereunto, the cytosolic soluble alanyl aminopeptidase (EC 3.4.11.14, puromycine-sensitive aminopeptidase, aminopeptidase PS, encephaline-degrading aminopeptidase) [A. J. Barret et al., a. a. O.].

Using the term "inhibitor" in the present description and in the claims such compounds of natural origin, synthetic origin or natural origin with synthetic modification are recognized having a regulatory, particularly inhibitory effect on an enzyme or a group of enzymes. The regulatory effect can be based on most different effects without limiting the aforementioned wide definition of the term "inhibitor". Preferred inhibitors according to the invention are inhibitors with an inhibitory effect on enzymes, more preferred on groups of enzymes for example inhibitors with inhibitory effect on dipeptidyl peptidase IV (DPIV) and on peptidases with dipeptidyl peptidase IV analogous enzymatic effect or inhibitors with inhibitory effect on alanyl aminopeptidase N (APN), respectively, and on peptidases with alanyl aminopeptidase N analogous enzymatic effect as defined above.

Using the term "precursor" in the present description and in the claims naturally occurring or synthetic or naturally occurring but synthetically modified compounds are recognized from which other compounds can be derived chemically under defined conditions. Hence inhibitor precursors are recognized to be compounds of natural or synthetic origin or natural but synthetically modified compounds which can react to inhibitors systematically.

Using the term "prodrug" in the present description and in the claims naturally occurring or synthetic or naturally occurring but synthetically modified compounds are recognized from which other compounds can be derived chemically under defined conditions preferably under physiological or pathological conditions whereat these other compounds develop a pharmacological effect which differs qualitatively and/or quantitatively of the starting substance. Hence inhibitor prodrugs are recognized to be compounds of natural or synthetic origin or natural but synthetically modified compounds which can react systematically preferably under physiological or pathological conditions, more preferred under physiological or pathological conditions in a mammal for example a human to new substances with inhibitory effect. This does not exclude that prodrugs per se are able, before being transformed into drugs with a defined pharmacological (for example inhibitory) effect, to develop a pharmacological effect (for example to inhibit one of the two afore-mentioned enzymes). Conditions of the transformation of prodrugs into drugs in a mammal or a human respectively can be of that ilk like they are regularly present in the physiological surroundings of a mammal for example a human or in the body of a mammal for example a human. Alternatively, such physiological conditions might only be present under defined conditions in a mammal as for example in a human like for example a defined physiological condition as present in for example a disease pattern or they can be induced or be invoked by external influences for example (without restriction) by medical influences to the organism of a mammal like for example the organism of a human being.

In the compounds of the afore-mentioned general formulae (1) and (2) A and A' which might be identical or different are a residue

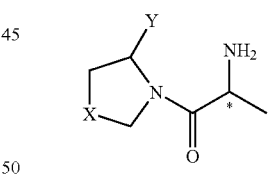

in which X is S, O, $CH_2$, $CH_2CH_2$, $CH_2O$, or $CH_2NH$ and Y is H or CN and * is a chiral carbon atom. Particularly preferred are according to the invention compounds or the general formula (1) in which A and A' are identical as well as compounds of the general formulae (1) and (2) in which the afore-mentioned A-representing residue X is S, $CH_2$ or $CH_2CH_2$ and/or Y is H or CN.

In further preferred embodiments of the invention such compounds of the general formulae (1) and (2) are prodrugs for particularly effective inhibitors in which the chiral carbon atom designated by * has either an S- or L-configuration.

In the compounds of the afore-mentioned general formulae (1) and (2) B and B' can be identical or different and are a residue containing an O, N or S containing or non-containing unsubstituted or substituted unbranched or branched alkylene-residue, cycloalkylene-residue aralalkylene-residue, heterocycloalkylene-residue, heteroarylalkylene-residue, arylamidoalkylene-residue, heteroarylamidoalkylene-residue, unsubstituted or mono- or polysubstituted arylene-residue or heteroaryl-residue having one or more five-, six-, or seven-membered ring(s).

Using the term "alkyl-residue" In the present description and in the claims a monovalent straight-chained ("unbranched") or branched residue made of carbon atoms linked by single bonds to each other with hydrogen atoms bound to the carbon atoms is recognized. Hence alkyl-residues are according to the present invention saturated monovalent hydrocarboned residues. Preferably the alkyl-residues in the compounds of the general formulae (1) and (2) comprise 1 to 18 carbon atoms and are thus selected from the residues methyl, ethyl, n-propyl, i-propyl and the numerous different straight-chained and branched isomers of the residues butyl, pentyl, hexyl, heptyl, octyl, nonyl, decyl, undecyl, dodecyl, tridecyl, tetradecyl, pentadecyl, hexadecyl, heptadecyl and octadecyl. Particularly preferred are straight-chained and branched alkyl-residues having 1 to 12 carbon atoms; straight-chained and branched alkyl-residues having 1 to 6 carbon atoms are even more preferred. Most preferred are residues methyl, ethyl, n-propyl, i-propyl, n-butyl, i-butyl, sec-butyl and tert-butyl.

Accordingly in the present description and in the claims the terms "alkenyl-residue" and "alkinyl-residue" monovalent straight-chained ("unbranched") or branched residues of carbon atoms linked to each other by single bonds and at least one double bond or triple bond, respectively at an arbitrary but defined position in the molecule with hydrogen atoms bound to the remaining bonds of the carbon atoms are recognized having at least 2 carbon atoms and up to 18 carbon atoms. Such residues are for example preferably vinyl-residues or allyl-residues; however, carbon-carbon multiple bond-containing residues are not restricted to said residues.

In the present descriptions and in the claims the term "alkylene-residue" is recognized to be a divalent straight-chained ("unbranched") or branched residue of carbon atoms linked to each other by single bonds with hydrogen atoms bound to the carbon atoms. Hence alkylene-residues are according to the present invention saturated divalent hydrocarbon-residues. Preferably alkylene-residues in the compounds of the general formulae (1) and (2) comprise 1 to 18 carbon atoms and are therefore selected from the residues methylene, ethylene, n-propylene, 2,2-propylene, 1,2-propylene and numerous different straight-chained and branched isomers of the residues butylene, pentylene, hexylene, heptylene, octylene, nonylene, decylene, undecylene, dodecylene, tridecylene, tetradecylene, pentadecylene, hexadecylene, heptadecylene and octadecylene. Particularly preferred are straight-chained and branched alkylene-residues having 1 to 12 carbon atoms and straight-chained and branched alkylene-residues having 1 to 6 carbon atoms are more preferred. Most preferred are the residues methylene, ethylene, n-propylene, 2,2-propylene, 1,2-propylene and the numerous different butylene-position isomers).

In the alkyl-residues and/or the alkylene-residues which can be according to the invention part of the compounds of the general formulae (1) and (2) the chains of carbon atoms might be interrupted by O-atoms, N-atoms or S-atoms; Hence in the course of the chain there might exist instead of one or more —CH$_2$-group(s) one or more group(s) of the group —O—, —NH— and —S—, whereas usually not two of the groups —O—, —NH— and/or —S— follow each other in the chain. Said one or more group(s) —O—, —NH— or —S— can be inserted at arbitrary positions in the molecule. Preferably if a hetero group of that ilk is present, a group of that ilk is present in the molecule.

Straight-chained as well as branched alkyl- or alkylene-residues might be substituted according to the invention in the compounds of the general formulae (1) and (2) in a further embodiment with one or more substituents preferably with one substituent. The substituent(s) can be located at arbitrary positions of the backbone, formed by the carbon atoms and can preferably, without restricting the invention hereunto, be selected from the group consisting of halogen atoms like fluorine, chlorine, bromine and iodine, particularly preferred chlorine and bromine, alkyl-groups having 1 to 6 C-atoms each, particularly preferred alkyl-groups having 1 to 4 C-atoms, alkoxy-groups having 1 to 6 C-atoms in the alkyl-residue preferably having 1 to 3 C-atoms in the alkyl-residue, unsubstituted or with one or two alkyl-residue(s) containing 1 to 6 C-atoms independently from each other, preferably 1 to 3 C-atoms, substituted amino-groups, carbonyl-groups and carboxyl-groups. The latter can also be present in form of salts or esters with alcohols having 1 to 6 carbon atoms in the alkyl-residue; hence the term "carboxyl-groups" includes groups of the general structure —COO$^-$ M$^+$ (with M=monovalent metal atom such as an alkali metal-atom or an accordant equivalent of a polyvalent metal atom such as half an equivalent of a divalent metal atom like an earth alkali metal atom) or of the general structure-COOR$_x$ (with R$_x$=alkyl-groups having 1 to 6 carbon atoms). The substituting alkyl-groups are selected from alkyl-groups mentioned above in detail and are particularly preferred methyl-groups, ethyl-groups, n-propyl-groups, i-propyl-groups, n-butyl-groups, i-butyl-groups, sec-butyl-groups or tert-butyl-groups. Alkoxygroups are alkyl-groups in the above-defined sense which are bound via an O-atom to the backbone formed by the carbon atoms. They are preferably selected from the group consisting of the residues methoxy, ethoxy, n-propoxy, i-propoxy; n-butoxy, i-butoxy, sec-butoxy and tert-butoxy. Amino-groups are groups of the general structure —NR$_x$R$_y$ in which the residues R$_x$ and R$_y$ might independently from each other designate, hydrogen or alkyl-groups (according to the afore-mentioned definition) having 1 to 6 carbon atoms particularly preferred having 1 to 3 C-atoms in which the residues R$_x$ and R$_y$ might be identical or different from each other. Such amino-groups being particularly preferred as substituents are —NH$_2$, —NH(CH$_3$), —N(CH$_3$)$_2$, —NH(C$_2$H$_5$) and —N(C$_2$H$_5$)$_2$. The term "amino-groups" contains also groups of the above-defined structure which are present as quaternated ammonium ions, either because of salt formation with organic acids or inorganic acids (e.g. residues of the structure R$_x$R$_y$R$^z$ N$^+$ Q$^-$, in which R$_x$, R$_y$ and R$_z$ might be identical or different preferably identical and R$_x$ and R$_y$ might have the above-defined meanings and at least one of the residues is hydrogen from the quaternation with the organic or inorganic acid and Q is an acid-residue from an acid of the organic or inorganic acid) or because of salt formation with suitable quaternation reagents which are known to a person skilled in the field such as (without restriction hereunto) with alkyl halogenids.

In the present description and in the claims the term "cycloalkyl" is used for unsubstituted or substituted monovalent residues of —CH$_2$-groups linked to each other in form of closed rings. According to the invention said rings might contain preferably 3 to 8 atoms forming the ring and might either contain exclusively carbon atoms or contain one or more hetero atom(s) which is/are selected from —O—, —S— and —NR$_x$— in which R$_x$ is hydrogen or a alkyl-residue (as defined above) having 1 to 6 carbon atoms. In case hetero atoms are inserted in the rings said hetero atoms can be—in case of more than one hetero atoms—identical or different. Preferably in case hetero atoms are present one hetero atom is inserted into the ring. Particularly preferred among purely carbocyclic rings are the residues cyclopentyl, cyclopentenyl, cyclopentadienyl, cyclohexyl, cyclohexenyl, cyclohexadienyl, cycloheptyl, cycloheptenyl, cyclohepadienyl and cycloheptatrienyl. Examples for hetero atoms containing cycloalkyl-residues which are often referred to as heterocycloalkyl-residues in further embodiments of the invention the residues tetrahydrofuranyl, pyrrolidinyl, pyrazolidinyl, imidazolidinyl, piperidinyl, piperazinyl and morpholinyl.

Possible substituents at the carbocyclic or heterocyclic cyloalkyl-residues might be preferably, without restricting the invention hereunto, selected from the afore-mentioned group of substituents for linear alkyl-groups. Particularly preferred substituents for cycloalkyl-groups are the substituents —Cl, —Br, -methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy and tert-butoxy, —NH$_2$, —NH(CH$_3$), —N(CH$_3$)$_2$, —NH(C$_2$H$_5$) and —N(C$_2$H$_5$)$_2$, carbonyl and carboxyl.

In the present description and in the claims the term "cycloalkylene" is used for unsubstituted or substituted divalent residues of —CH$_2$-groups linked to closed rings. According to the invention these can preferably contain three to eight atoms in the ring and can consist either exclusively of carbon atoms or contain one or more hetero atom(s) which is/are selected from —O—, —S— and —NR$_x$—, in which R$_x$ is hydrogen or a alkyl-residue (as defined above) having 1 to 6 carbon atoms. Particularly preferred among the purely carbocyclic rings are the residues cyclopentylen, cyclopentenylen, cyclopentadienylen, cyclohexylen, cyclohexenylen, cyclohexadienylen, cycloheptylen, cycloheptenylen, cycloheptadienylen and cycloheptatrienylen. Also, the heterocyclic groups defined above with regard to the cycloalkyl-residues can appear in compounds of the general formulae (1) and (2) as groups "B" in form of divalent residues and particularly preferred are such cyclic divalent residues in which one group —O— or —NR$_x$— is inserted into the ring. In those cases both valences are localized at arbitrary C-atoms in the ring. Preferably one hetero atom or two hetero atom(s) is/are inserted into the ring and in particularly preferred embodiments of such groups the divalent residues are derived from tetrahydrofuran, pyrrolidin, pyrazolidin, imidazolidin, piperidin, piperazin and morpholin.

Possible substituents at these carbocyclic or heterocyclic cycloalkylene-residues can be preferably, without restricting the invention hereunto, selected from the afore-mentioned group of substituents for linear alkyl-groups. Particularly preferred substituents for cycloalkylene-groups are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy and tert-butoxy, —NH$_2$, —NH(CH$_3$), —N(CH$_3$)$_2$, —NH(C$_2$H$_5$) and —N(C$_2$H$_5$)$_2$, carbonyl and carboxyl.

Using the term "aryl-residue" in the present description and in the claims a monovalent hydrocarbon-residue is recognized which is derived from a cyclic molecule with aromatic character (4n+2 in ring orbitals delocalized π-electrons) which might be unsubstituted or substituted. The ring structure of such an aryl-residue can be a five-, six- or seven-membered ring structure with one ring or a structure formed by two or more ("annelated") rings bound to each other whereat the annelated rings have identical or different numbers of ring members, particularly of C-atoms. In case of systems consisting of more than one rings condensated to each other, benzocondensated rings are particularly preferred, i.e. a ring system in which at least one of the rings is an aromatic, exclusively C-atoms containing six-membered ring (phenyl ring). Typical but not limiting examples of aryl rings are cyclopentadienyl-residues (C$_5$H$_5^-$) (being a five-membered ring), phenyl-residues (being a six-membered ring), cycloheptatrienyl-residues (C$_7$H$_7^+$) (being an seven-membered ring) naphthyl-residues (being a ring system comprising two annelated six-membered rings) as well as monovalent residues being derived from anthracen and phenanthren (being three annelated six-membered rings). According to the invention most preferred aryl-residues are phenyl- and naphthyl-residues.

Possible substituents of carbocyclic aryl-residues can be selected preferably from the groups of substituents mentioned above for linear alkyl-groups, without restricting the invention to theses substituents. Particularly preferred substituents for aryl-groups are substituents —Cl, —Br, -methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy and tert-butoxy, —NH$_2$, —NH(CH$_3$), —N(CH$_3$)$_2$, —NH(C$_2$H$_5$) and —N(C$_2$H$_5$)$_2$, carbonyl and carboxyl. One or more substituent(s) of this ilk which might be identical or different from each other can be bound to one aryl-residue according to the present invention. The substituted position(s) at the aryl-ring (-system) can be chosen arbitrarily.

A comparable definition as in case of the aryl-residues applies to the present description and the claims with regard to the definition of the term "arylene-residue": in this regard a divalent residue is recognized which elementary composition the selection thereof and the substituent(s) thereof are comparable with the afore-mentioned definitions of the aryl-residues with the exception that it is a divalent residue which insertion can be carried out at two arbitrary carbon atoms.

In the present description and in the claims the term "heteroaryl-residue" an aryl-residue is recognized (in accordance with the afore-mentioned definition) which ring structure contains one or more hetero atom(s) preferably from the group O, N or S without losing the aromatic character of the molecule. Heteroaryl-residues can be unsubstituted or substituted according to the invention. The ring structure of such a heteroaryl-residue can either be a five-membered, a six-membered or a seven-membered ring structure with one ring or be a structure formed by two or more ("annelated") rings bound to each other wherein the annelated rings might have an identical or a different number of ring members. The hetero atom(s) can occur in one ring alone or in more than one ring of the ring system. The heteroaryl-residues preferably consist of one or two rings. In case of systems consisting of more than one ring condensated to each other, benzocondensated rings are especially preferred, i.e. ring systems in which at least one of the rings is an aromatic carbocyclic (i.e. only C-atoms containing) six-membered ring. Particularly preferred heteroaryl-residues are selected from furanyl, thiophenyl, pyridyl, indolyl, cumaronyl, thionaphthenyl, chinolinyl (benzopyridyl), chinazolinyl (bezopyrimidinyl) and chinoxylinyl (benzopyrazinyl).

Possible substituents at these heteroaryl-residues can be preferably selected from the afore-mentioned group of substituents for linear alkyl-groups without restricting the invention to these substituents. Particularly preferred substituents for heteroaryl-groups are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy, tert-butoxy, —NH$_2$, —NH(CH$_3$), —N(CH$_3$)$_2$, —NH(C$_2$H$_5$) and —N(C$_2$H$_5$)$_2$, carbonyl and carboxyl. One or more substituents of that ilk which might be identical or different from each other might be bound to one heteroaryl-residue according to the present invention. The substituted position(s) at the heteroaryl-ring (-system) can be selected arbitrarily.

A comparable definition as in the case of the heteroaryl-residues applies to the present description and the claims with regard to the definition of the term "heteroarylene-residue": in this regard a divalent residue is recognized which general composition and which selection and which substituents are comparable to the afore-mentioned definition of "heteroaryl-residues" with the exception that it is a divalent residue which insetion can be carried out at two arbitrary carbon atoms of the ring or the ring system respectively or at a nitrogen atom as well.

In the context of the present description and in the claims the terms "aralkyl-residue", "heteroarylalkyl-residue", "heterocycloalkyl-residue", "arylamidoalkyl-residue" and heteroarylamidoalkyl-residue", mean alkyl-residues (—or more specifically—alkylene-residues) according to the afore-mentioned general and specific definition which are substituted at one of their bonds with an aryl-residue (according to the afore-mentioned general and specific definition), hetroaryl-residue (according to the afore-mentioned general and specific definition), heterocyclyl-residue (according to the afore-mentioned general and specific definition of the cycloalkyl-residues substituted with hetero atoms) arylamido-residues (according to the following general and specific definition) or heteroarylamido-residue (according to the following general and specific definition). These residues can be unsubstituted or substituted.

In preferred embodiments of the invention aralkyl-residues are residues of that ilk, in which the aryl-residue is a phenyl-residue, substituted phenyl-residue, naphthyl-residue or substituted naphthyl-residue and the alkyl(ene)-group is straight-chained or branched having 1 to 6 carbon atoms. In a very particular and advantageous way the residues benzyl, phen-ethyl, naphthylmethyl and naphthylethyl can be used as aralkyl-residues of which benzyl-residues are particularly preferred.

Possible substituents at the aryl-groups of the aralkyl-residues can be preferably selected from the afore-mentioned group of substituents for linear alkyl-groups without restricting the invention to those substituents. Particularly preferred substituents for aryl-groups of the aralkyl-residues are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy, tert-butoxy, —NH$_2$, —NH(CH$_3$), —N(CH$_3$)$_2$, —NH(C$_2$H$_5$) and —N(C$_2$H$_5$)$_2$, carbonyl and carboxyl. One or more substituents of that ilk which might be identical or different from each other can be bound to one aryl-group of an aralkyl-residue according to the present invention. The substituted position(s) at the aryl ring (-system) can be chosen arbitrarily.

In preferred embodiments of the invention the heteroalkyl-residues are such residues in which the heteroaryl-residue of the heteroarylalkyl-residue according to the invention is substituted and the alkylene-group is straight-chained or branched having 1 to 6 carbon atoms. The ring structure of such a heteroaryl-residue can be a ring structure with one ring or a structure formed by two or more than two ("annelated") rings bound to each other wherein the annelated rings might have an identical or different number of ring members. The hetero atom(s) can occur in one or more ring(s) of the ring system. The heteroaryl-residues of the heteroarylalkyl-residue consist preferably of one or two rings. In case of heteroarylalkyl systems composed of more than one rings condensated to each other, benzocondensated rings are especially preferred, i.e. ring systems in which at least one of the rings is an aromatic carbocyclic six-membered ring. Particularly preferred heteroaralalkyl-residues are selected from furanylm-ethyl and -ethyl, thiophenylmethyl and -ethyl, pyridylmethyl and ethyl, indolylmethyl and -ethyl, cumaronylmethyl and -ethyl, thionaphthenylmethyl and -ethyl, chinolinyl-(bezopy-ridyl-)methyl and -ethyl, chinazolinyl-(benzopyrimidinyl-) and chinoxylinyl-(benzopyrazinyl-)methyl and -ethyl.

Possible substituents at these heteroaryl-groups of heteroarylalkyl-residues can be preferably selected from the afore-mentioned group of substituents for linear alkyl-groups without restricting the invention to thereunto. Particularly preferred substituents for heteroaryl-groups are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy, tert-butoxy, —NH$_2$, —NH(CH$_3$), —N(CH$_3$)$_2$, —NH(C$_2$H$_5$) and —N(C$_2$Hs)$_2$, carbonyl and carboxyl. One or more substituent(s) of that ilk which can be identical or different from each other can be bound to a heteroarylalkyl-residue according to the present invention. The substituted position(s) at the heteroaryl ring (-system) can be chosen arbitrarily.

In preferred embodiments of the invention heterocycloalkyl-residues are cycloalkyl-residues according to the afore-mentioned general and specific definition which contain one or more hetero atom(s) which is/are selected from —O—, —S— and —NR$_x$—, in which R$_x$ is hydrogen or an alkyl-residue having 1 to 6 carbon atoms (as defined above) and the alkyl(ene)-groups of the heterocycloalkyl-residues are straight-chained or branched having 1 to 6 carbon atoms. In case of more than one hetero atoms inserted into the ring(s) these can be identical or different. Preferably one hetero atom is incorporated in the ring. Preferred examples for hetero atoms containing cycloalkyl-residues which are also referred to as heterocycloalkyl-residues are in further embodiments of the invention the residues tetrahydrofuranyl, pyrrolidinyl, pyrazolidinyl, imidazolidinyl, piperidinyl, piperazinyl and morpholinyl.

Possible substituents at these heterocycloalkyl-residues can preferably be selected from the afore-mentioned group of substituents for linear alkyl-groups, without restricting the invention to those substituents. Particularly preferred substituents for heteroaryl-groups are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy, tert-butoxy, —NH$_2$, —NH(CH$_3$), —N(CH$_3$)$_2$, —NH(C$_2$H$_5$) and —N(C$_2$H$_5$)$_2$, carbonyl and carboxyl. One or more substituent(s) of that ilk which might be identical or different from each other can be bound to one heterocycloalkyl-residue according to the present invention. The substituted position(s) at the heterocacloalkyl-ring (-system) can be chosen arbitrarily.

Using the terms "arylamidoalkyl-residue" and "heteroarylamidoalkyl-residue" in the present description and in the claims alkyl-residues (—more precisely—alkylene-residues) according to the afore-mentioned general and specific definition are recognized which are substituted at one of their bonds by an arylamido-residue or heteroarylamido-residue of the general formula Ar—NR$_x$—C(=O)— or the general formula Ar—C(=O)—NR$_x$— in which R$_x$ is hydrogen or an alkyl having 1 to 6 carbon atoms and Ar is an arbitrary aryl-residue or heteroaryl-residue according to the afore-mentioned general or specific definition. These aryl- or heteroaryl-residues can be unsubstituted or substituted. Preferred examples for an arylamidoalkyl-residue—without restricting the invention—are 2-, 3- or 4-benzoe-acid-amino-n-butyl-residues or 2-nitro-3-, -4-, -5- or -6-benzoe-acid-amido-n-butyl-residues; preferred but not limiting examples for heteroarylamidoalkyl-residues are 2-, 4-, 5- or 6-pyridin-3-carbonacid-amido-n-butyl-residues.

Possible substituents at these arylamidoalkyl-residues and heteroarylamidoalkyl-residues can preferably be selected from the afore-mentioned group of substituents for linear alkyl-groups, without restricting the invention to those substituents. Particularly preferred substituents for aryl-groups or heteroaryl-groups of the arylamidoalkyl-residues and heteroarylamidoalkyl-residues are the substituents —Cl, —Br, methyl, ethyl, n-propyl, i-propyl, n-butyl, i-butyl, sec-butyl or tert-butyl, methoxy, ethoxy, n-propoxy, i-propoxy; n-butoxy, i-butoxy, sec-butoxy, tert-butoxy, —NH$_2$, —NH(CH$_3$), —N(CH$_3$)$_2$, —NH(C$_2$H$_5$) and —N(C$_2$H$_5$)$_2$, carbonyl and carboxyl. One or more substituent(s) of that ilk which can be identical or different from each other can be bound to an aryl- or heteroaryl-group of the arylamidoalkyl-residues or heteroarylamidoalkyl-residues according to the present invention. The substituted position(s) at the aromatic ring (-system) can be chosen arbitrarily.

A comparable definition as for the aralkyl-residues, heteroarylalkyl-residues, heterocycloalkyl-residues, arylamidoalkyl-residues and heteroarylamidoalkyl-residues applies in the context of the present description and the claims with regard to the definition of the terms "aralkylene-residue", "heteroarylalkylene-residue", "heterocycloalkylene-residue", "arylamidoalkylene-residue" and "heteroarylamidoalkylene-residue": These are understood to be divalent residues which general composition and the selection thereof and the substituent(s) thereof are comparable to the afore-mentioned definition of "aralkyl-residue", "heteroarylalkyl-residue", "heterocycloalkyl-residue", "arylamidoalkyl-residue" and "heteroarylamidoalky-residue" with the exception that it is in either case a divalent residue which insertion can be carried out at two arbitrary carbon atoms of the ring or the ring system of the alkylene-group respectively, or also at a nitrogen atom of the heteroaryl or heterocyclyl ring system.

In the general formulae (1) and (2) the residue D is —S—S— or —Se—Se—. These two S- or Se-atoms respectively, form a bridge between two parts of the molecules of the compounds of the general formulae (1) and (2) which can be cleaved under natural, particularly under reducing conditions. Thereby two parts of the molecule are released which develop an inhibitory effect on dipeptidyl peptidase IV (DPIV) and on peptidases with analogous enzymatic effect as well as on alanyl aminopeptidase N (APN) and on peptidases with analogous enzymatic effect.

In the afore-mentioned general formula (2) E is the group —CH$_2$—C*H(NH$_2$)—R$^9$ in which R$^9$ is an O, N or S containing or non-containing unsubstituted or substituted unbranched or branched alkyl-residue, cycloalkyl-residue, aralkyl-residue, heterocycloalkyl-residue, heteroarylalkyl-residue, arylamidoalkyl-residue, heteroarylamidoalkyl-residue, unsubstituted or mono-substituted or polysubstitued aryl-residue or heteroaryl-residue with one or more five-, six- or seven-membered ring(s). With regard to the inventory-conform usable or preferred examples of the alkyl-residues, cycloalkyl-residues, arylalkyl-residues, heterocycloalkyl-residues, heteroarylalkyl-residues, arylamidoalkyl-residues, heteroarylamidoalkyl-residues, unsubstituted or mono- or poly-substituted aryl-residues or heteroaryl-residues with one or more five-, six-, or seven-membered ring(s) as well as with regard to conceivable and preferred substituents for these residues it can be referred to the afore-mentioned definitions of the accordant residues and their preferred embodiments; these definitions are identically applicable for the residues of general formula (2) designated by E.

In said formula for E, the carbon atom, which is substituted with the amino-group is a chiral carbon atom, symbolized by *. In a further preferred embodiment of the invention such compounds of general formula (2) are prodrugs for particularly effective inhibitors in which the chiral carbon atom designated by * has either an S- or an L-configuration.

According to the invention E preferably designates 2-aminoalkylene-residues, for example a 2-amino-3-phenylpropyl-residue or an unsubstituted or by hetero atoms such as —S—, —S(=O)—, —N— or —O-substituted 2-aminoalkylene-residues, for example a 2-amino-4-methylpentyl-residue, a 2-amino-4-methylthiobutyl-residue or a 2-amino-4-methyl-sulfoxybutyl-residue.

In further preferred embodiments of the invention the residues B and/or B' are in the general formulae (1) and (2) a residue R$^1$ which is a straight-chained or branched alkylene-residue having 1 to 6 carbon atoms. Particularly preferred compounds of the general formulae (1) and (2) comprise residues B and/or B' in form of one or more of the group(s) selected from —CH$_2$-(methylene), —CH$_2$—CH$_2$(ethylene) or (H$_3$C)$_2$—C<(2,2-propylene).

In alternative also further preferred embodiments B and/or B' is a residue —(CH$_2$)$_n$—R$^2$—R$^3$—R$^4$—, in which n is an integer from 1 to 5; R$^2$ is —NH— or —NH—C(=NH)—NH—, if R$^3$ is O=C< or —SO$_2$— or in which R$^3$ is O=C< if R$^3$ is —NH—; R$^4$ is O, N or S containing or non-containing unsubstituted or substituted unbranched or branched alkylene-residue, cycloalkylene-residue, arylalkylene-residue, heterocycloalkylene-residue, heteroarylalkylene-residue, unsubstituted or mono-substituted or poly-substituted arylene-residue or heteroarylene-residue with one or more five-, six- or seven-membered ring(s). Further preferred, n is an integer from 1 to 5, so that preferred examples of the afore-mentioned residues contain a methylene-group, ethylene-group, propylene-group, butylene-group and pentylene-group; R$^2$ and R$^3$ in combination preferably form an amido-group —C(=O)—NH— or —NH—C(=O)—. Further preferred are such compounds of the general formulae (1) and (2) with residues B and/or B' in which B is the afore-mentioned formula and R$^4$ is an amino-substituted alkylene-residue, for example an aminoethylene-residue or an unsubstituted or (for example by a nitro-group) substituted phenylene-residue or an unsubstituted or substituted pyridyl-2,5-ene-residue.

In alternative also further preferred embodiments B and/or B' is a residue of the formula —R$^7$-R$^8$—, in which R$^7$ is a mono- or poly-substituted benzylene residue and R$^8$ is a single bond or an O, N or S containing or non-containing unsubstituted or substituted unbranchend or branched alkylene residue, cycloalkylene residue, aralalkylene residue, heterocycloalkylene residue or heteroarylalkylene residue, which might contain as functional groups preferably one or more amino groups, carbonyl groups or carboxyl groups or an unsubstituted or mono- or poly-substituted arylene residue or heteroarylene residue with one or more five-, six-, or seven-membered ring(s). With regard to the definition of the afore-mentioned residues and their conceivable inventory substituents it can be referred to the afore-mentioned general or specific definition of the particular residues or substituents.

Further preferred are according to the invention compounds of the general formulae (1) or (2) in which B and B' might be identical or different and which designate a residue —(CH$_2$)$_n$—R$^2$—R$^3$—R$^4$ in which R$^2$ is —NH— or —NH—C(=NH)—NH— if R$^3$ is O=C< or —SO$_2$— or in which R$^2$ is O=C< if R$^3$ is —NH— and in which R$^4$ is —CH (COOH)—R¹—, in which R¹ has the afore-mentioned meaning if R² is O=C< and R³ is —NH—; or

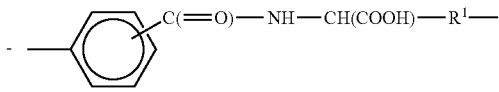

(substitution at position 2, 3 or 4) in which R¹ has the afore-mentioned meaning if R² is O=C< and R³ is —NH—; or —CH(NHR⁵)—R¹— if R² is —NH— or —NH—C(=NH)—NH— and R³ is O=C< in which R⁵ is H or an acyl residue preferably a benzyloxycarbonyl residue, a fluorene-9-ylmethoxycarbonyl residue, a tert-butyloxycarbonyl residue or a benzoyl residue; or

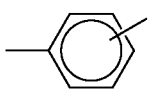

—(substitution at position 2, 3 or 4), in which R⁴ is phenylene and R² is —NH— or —NH—C(=NH)—NH— if R³ is O=C< or —SO₂— or in which R² is O=C< if R³ is —NH—; or

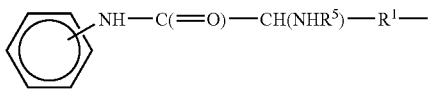

(substitution at position 2, 3 or 4) in which R⁵ is H or an acyl residue preferably a benzyloxycarbonyl residue, a fluoren-9-ylmethoxycarbonyl residue or a benzoyl residue and R² is —NH— or —NH—C(=NH)—NH— if R³ is O=C< or —SO₂— or in which R² is O=C< if R³ is —NH—; or

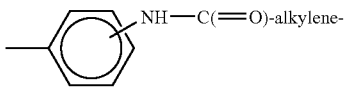

(substitution at position 2, 3 or 4), in which alkylene is an unbranched or branched alkylene residue having 1 to 6 carbon atoms and R² is —NH— or —NH—C(=NH)—NH— if R³ is O=C< or —SO₂— or in which R² is O=C< if R³ is —NH—; or

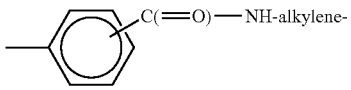

(substitution at position 2, 3 or 4), in which alkylene is an unbranched or branched alkylene residue having 1 to 6 carbon atoms and R² is —NH— or —NH—C(=NH)—NH— if R³ is O=C< or —SO₂— or in which R² is O=C< if R³ is —NH—; or

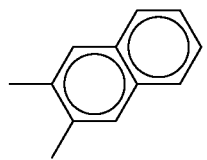

in which and R² are —NH— or —NH—C(=NH)—NH— if R³ is O=C< or —SO₂— or in which R² is O=C< if R³ is —NH—; or

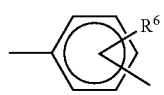

(substitution at position 2, 3 or 4)

(substitution at the ring depending on the position of R⁶) in which R⁶ is H, NO₂, CN, halogen or an acyl residue and R² is —NH— or —NH—C(=NH)—NH— if R³ is O=C< or —SO₂— or in which R² is O=C< if R³ is —NH—; or

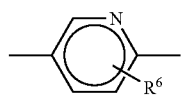

(substitution at position 3, 4 or 6), in which R⁶ is H, NO₂, CN, halogen or an acyl residue and R² is —NH— or —NH—C(=NH)—NH— if R³ is O=C< or —SO₂— or in which R² is O=C< if R³ is —NH—; or

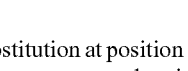

(substitution at position 4, 5 or 6), in which R⁶ is H, NO₂, CN, halogen or an acyl residue and R² is —NH— or —NH—C(=NH)—NH— if R³ is =C< or —SO₂— or in which R² is O=C< if R³ is —NH; or

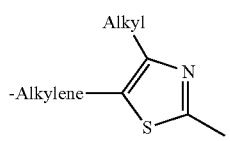

in which and R² is —NH— or —NH—C(=NH)—NH— if R³ is O=C< or —SO₂— or in which R² is O=C< if R³ is —NH—.

Alternatively thereto according to the invention compounds of the general formulae (1) and (2) are further preferred, in which B and B' may be identical or different and designate a residue —R⁷-R⁸— in which R⁷ and R⁸ in combination are a residue

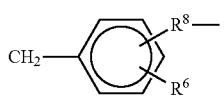

(in which R⁷ is the residue above without R⁸ and in which the position of R⁶ is dependent of the position R⁸) in which R⁸ and R⁶ have the afore-mentioned meanings, i.e. in which R⁶ is H, NO₂, CN, halogen or an acyl residue and in which R⁸ is a single bond or an O, N or S containing or non-containing unsubstituted or substituted unbranched or branched alkylene residue, cycloalkylene residue, aralkylene residue, heterocycloalkylene residue or heteroarylalkylene residue which preferably contains as functional groups one or more amino-group(s), carbonyl group(s) or carboxyl group(s) or which is unsubstituted or mono- or poly-substituted arylene residue or heteroarylene residue with one or more five-, six- or seven-membered ring(s).

Further preferred compounds of the general formulae (1) and (2) are such in which B and B' are identical or different and designate independently from each other a residue —R⁷-R⁸— in which R⁷ is a mono- or poly-substituted benzylene residue of the afore-mentioned formula (without R⁸) and R⁸ is
  —NH— or —C₁- to C₆-alkylene-NH— in combination with
    —C(=O)—C₁- to C₆-alkylene- or
    —C(=O)-arylene- or
    —SO₂—C₁- to C₆-alkylene- or
    —SO₂-arylene- or

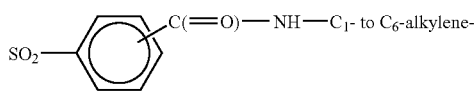

(substitution at position 2, 3 or 4) or
    —C(=O)—CH(NHR⁵)—R¹ in which R¹ and R⁵ have the afore-mentioned meanings; or
  O=C< in combination with
    —NH—C₁- to C₆-alkylene- or
    —NH-arylene- or
    —NH—CH(COOH)—R¹— in which R¹ has the afore-mentioned meanings; or
    —O—C₁- to C₆-alkylene- or
    —O-arylene- or
    —O—C₁- to C₆-alkylene-NH—C(=O)—CH(NH₂)—R¹— in which R¹ has the afore-mentioned meanings, or
    —O—C₁- to C₆-alkylene-C(=O)—NH—CH(COOH)—R¹—, in which R¹ has the afore-mentioned meanings.

According to the invention the compounds of the general formulae (1) and/or (2) are present in form of neutral molecules and are according to the invention used as neutral molecules. Alternatively to that the compounds of the general formulae (1) and/or (2) can also be present in form of their acid addition salts with inorganic and/or organic acids. Because of the presence of alkaline centers (mostly of alkaline nitrogen atoms) in the molecule such acid addition salts are formed by the addition of one or more molecules of H-acid compounds (Brönstedt acids) preferably one molecule of an H-acid compound and provide an improved solubility of the molecules on polar media like for example in water. The latter characteristic is of particular impact for such compounds which develop pharmacological effect.

In preferred embodiments of the invention acid addition salts are salts of pharmaceutically acceptable acids and are advantageously chosen (but without limiting the present invention) from the group consisting of hydrochlorides, trifluoroacetates, tartrates, succinates, formiates and/or citrates of the compounds of the general formulae (1) or (2).

Particularly preferred and advantageously usable compounds of the general formula (1) are characterized by the general formula (1a)

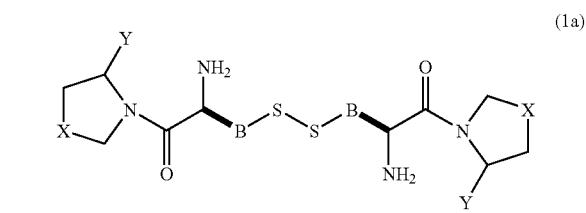

(1a)

in which X, Y and B have the afore-mentioned meanings. With particular advantage usable and thus subject of the invention are acid addition salts of the compound of the general formulae (1a) preferably the acid addition salts with pharmaceutical acceptable inorganic and/or organic acids thereof particularly with acids of the afore-mentioned group.

Exceptionally advantageous compounds of the general formula (1a) result from the following table 1 without restricting the invention to those compounds:

TABLE 1

Examples of compounds of general formula A-B-D-B'-A' (1)

| No. | B | X | Y |
|---|---|---|---|
| I | ━CH₂— | —CH₂— | H |
| II | ━CH₂— | S | H |
| III | ━CH₂— | —CH₂— | CN |
| IV | ━(CH₂)₄—NH—C(=O)—CH(NH₂)—CH₂— | S | H |
| V | ━(CH₂)₄—NH—C(=O)—[3-methyl-6-nitrophenyl]— | S | H |
| VI | ━(CH₂)₄—NH—C(=O)—[6-methylpyridin-3-yl]— | S | H | and the acid addition salts thereof preferably the acid addition salts thereof having pharmacologically acceptable inorganic and/or organic acids preferably from the afore-mentioned groups of pharmacologically acceptable acids.

Particularly preferred and advantageously usable compounds of the general formula (2) are characterized by the general formula (2a).

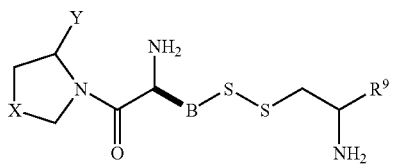
(2a)

in which X, Y, R⁹ and B have the afore-mentioned meanings and the acid addition salts thereof preferably the acid addition salts thereof with pharmaceutically acceptable inorganic and/or organic acids preferably from the afore-mentioned group of pharmaceutically acceptable acids.

Exceptionally preferred compounds of the general formula (2a) result from following table 2 without restricting the invention to theses compounds:

TABLE 2

| | Examples of compounds of general formula A-B-D-E (2) | | | | |
|---|---|---|---|---|---|
| No. | B | $R^9$ | X | Y | Empirical formula |
| VII | —CH₂— | —CH₂—C₆H₅ | S | H | $C_{15}H_{23}N_3OS_3$ |
| VIII | —C(CH₃)₂CH₃ (tert-butyl) | —CH₂—C₆H₅ | S | H | $C_{17}H_{27}N_3OS_3$ |
| IX | —(CH₂)₄—NH—C(O)—(2-NO₂-4-methylphenyl) | —CH₂—C₆H₅ | S | H | $C_{25}H_{33}N_5O_4S_3$ |
| X | —(CH₂)₄—NH—C(O)—(6-methylpyridin-3-yl) | —CH₂—C₆H₅ | S | H | $C_{24}H_{33}N_5O_2S_3$ |
| XI | —(CH₂)₄—NH—C(O)—C₆H₄—CH₂—NH—C(O)—CH(NH₂)—CH₂— | —CH₂—C₆H₅ | S | H | $C_{29}H_{42}N_6O_3S_3$ |
| XII | —(CH₂)₄—NH—C(O)—C₆H₄—NH—C(O)—CH(NH₂)—CH₂— | —CH₂—C₆H₅ | S | H | $C_{28}H_{40}N_6O_3S_3$ |
| XIII | —CH₂—C₆H₄—NH—C(O)—CH(NH₂)—CH₂— | —CH₂—C₆H₅ | S | H | $C_{24}H_{33}N_5O_2S_3$ | and the acid addition salts thereof preferably the acid addition salts thereof with pharmaceutically acceptable inorganic and/or organic acids.

The invention also relates to a process to prepare compounds of the general formulae A-B-D-B'-A'  (1) and

A-B-D-E  (2).

In said formulae (1) and (2) A, A', B, B', D and E have the meanings mentioned above in detail. With regard to the process of the preparation of the new compounds (1) and/or (2) according to the afore-mentioned scheme of synthesis 1 either compounds of the general formula

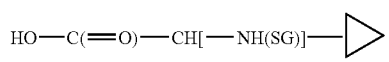

in which (SG) is a protecting group and

is a structure element of B are transformed with a heterocyclic compound of the general formula

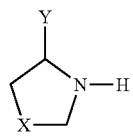

in which X is S, O, $CH_2$, $CH_2CH_2$, $CH_2O$ or $CH_2NH$ and Y is H or CN; the obtained condensation product of the formula

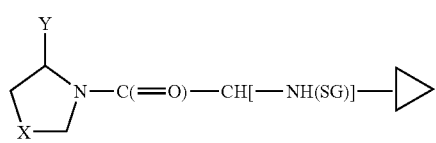

is transformed with a compound of the general formula

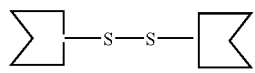

in which

is a structure element of B; and the resulting reaction product is transformed being cleaved from the protecting group (SG) into a compound of the general formula A-B-D-B'-A' (1) in which A and A' may be identical or different and B and B' may be identical or different and in which A, A', B, B' and D may have the afore-mentioned meanings; or compounds of the general formula

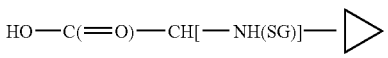

in which (SG) is a protecting group and

is a structure element of B are transformed with a heterocyclic compound of the general formula

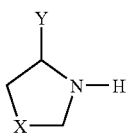

in which X is S, O, $CH_2$, $CH_2CH_2$, $CH_2O$ or $CH_2NH$ and Y is H or CN; the resulting condensation product of the formula

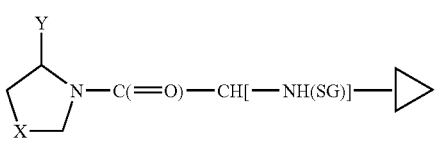

is transformed with a compound of the general formula

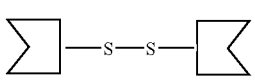

in which

is a structure element of B; and the resulting reaction product is transformed with a compound of the general formula

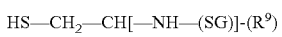

HS—$CH_2$—CH[—NH—(SG)]-($R^9$)

and is transformed being cleaved from the protecting groups (SG) into a compound of the general formula A-B-D-E (2), in which A, B, D and E may have the afore-mentioned meanings; or a compound of the general formula

in which (SG) is a protecting group,

is a structure element of B and Z is a residue, which activates an —S—S-group for a thiol exchange, is transformed with a heterocyclic compound of the general formula

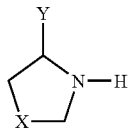

in which X is S, O, CH$_2$, CH$_2$CH$_2$, CH$_2$O or CH$_2$NH and Y is H or CN; the obtained condensation product of the formula

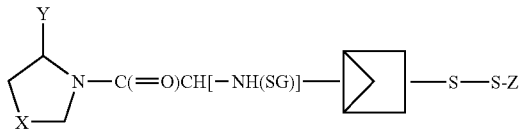

is transformed with a compound of the general formula

HS—CH$_2$—CH[—NH—(SG)]-(R$^9$) 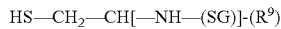

and is transformed being cleaved from the protecting groups (SG) into a compound of the general formula A-B-D-E (2), in which A, B, D and E may have the afore-mentioned meanings; or
a compound of the general formula

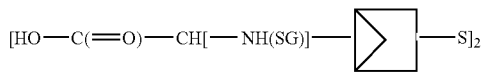

in which SG is a protecting group and

is a structure element of B is transformed with a heterocyclic compound of the general formula

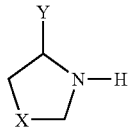

in which X is S, O, CH$_2$, CH$_2$CH$_2$, CH$_2$O or CH$_2$NH and Y is H or CN; and the obtained reaction product is transformed with a compound of the general formula HS—CH$_2$—CH[—NH—(SG)]-R$^9$ 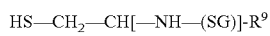

into a compound of the general formula A-B-D-E (2) in which A, B, D and E may have the afore-mentioned meanings; or
a compound of the general formula

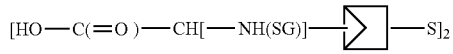

in which SG is a protecting group and

is a structure element of B, is transformed with a heterocyclic compound of the general formula

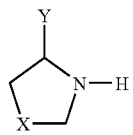

in which X is S, O, CH$_2$, CH$_2$CH$_2$, CH$_2$O or CH$_2$NH and Y is H or CN; and the obtained reaction product is cleaved from the protecting groups into a compound of the general formula A-B-D-B'-A' (1) in which A and A' may be identical or different and B and B' may be identical or different and in which A, A', B, B' and D may have the afore-mentioned meanings or compounds of the general formula

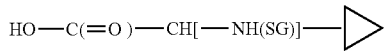

in which (SG) is a protecting group and

is a structure element of B are transformed with a heterocyclic compound of the general formula

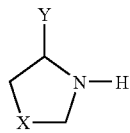

in which X is S, O, CH$_2$, CH$_2$CH$_2$, CH$_2$O or CH$_2$NH and Y is H or CN; the obtained condensation product of the formula

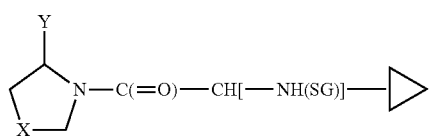

is transformed with a compound of the general formula

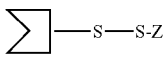

in which

is a structure element of B and Z is a residue which activates an —S—S-group for a thiol exchange and (SG) is a protecting group; and the obtained reaction product of the formula

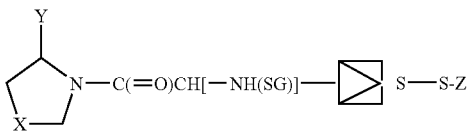

is transformed with a compound of the general formula

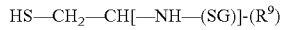

and is transformed being cleaved from the protecting group (SG) into a compound of the general formula A-B-D-E (2) in which A, B, D and E may have the afore-mentioned meanings.

Protecting groups which have been inserted in the context of the afore-mentioned process steps into the intermediate of the synthesis of compounds of the general formulae (1) and (2) ("SG") can be arbitrary protecting groups which are known to a person in the field of organic synthesis from his practical experience and they are according to the invention not restricted. Preferred protecting groups are protecting groups for protecting amino acid side-chains such as urethane protecting groups for example benzyloxycarbonyl-residues, fluorene-9-ylmethoxycarbonyl-residues, tert-butyloxycarbonyl-residues etc.

The groups Z which have been inserted in the context of the afore-mentioned process steps into intermediates of the synthesis of compounds of the general formulae (1) and (2) are residues which activate a molecule containing an S—S-group for a thiol-exchange, hence an exchange of a group bound to the S-atom for an S-atom (optionally attached to a substituent) of another molecule. Such groups are sufficiently known to a person skilled in the field of organic synthesis and the invention is not restricted to certain groups which activate for a thiol-exchange. Preferred but not restricting examples are the groups 3-nitro-2-pyridyl, 5-nitro-2-pyridyl, 2-, 3- or 4-pyridyl, 2-nitrophenyl, methoxycarbonyl or N-methyl-N-phenylcarbamoyl.

The symbols

used in the general reaction scheme for the synthesis leading to compounds of the general formulae (1) and (2) and also used in the afore-going and in the following descriptions of process steps mean structure elements of the residues B or B', respectively, in the compounds of the general formulae (1) and (2). Using the term "structure elements" it is understood in this context that the residues B or B', respectively are composed of parts of the molecule having a reactive group each which is added in the context of an organic synthesis forming a covalent bond between the two reactive groups which become thereby adjacent bond partners in the newly formed molecule. Particular but not restricting examples for such structure elements are a carboxyl-group in one and a hydroxy-group in the second molecule which add to one another forming an ester-group and releasing water or a carboxyl-group in one and an amino-group in the second molecule which add to one another forming an amido-group and releasing water. This is symbolized by the combination of the two symbols shown above on the left to give the symbol shown above on the right.

With particular advantage the compounds (1) and/or (2) can be prepared in processes which are presented in the following schemes of synthesis 2 to 17:

A compound of the general formulae

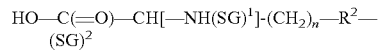

in which $(SG)^1$ is a protecting group for an amino-group, $(SG)^2$ is a protecting group at the substituent $R^2$ and $R^2$ and n have the afore-mentioned general or specific meanings, is transformed with a heterocyclic compound of the general formula

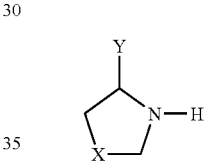

in which X is S, O, $CH_2$, $CH_2CH_2$, $CH_2O$ or $CH_2NH$ and Y is H or CN; the resulting condensation product of the formula

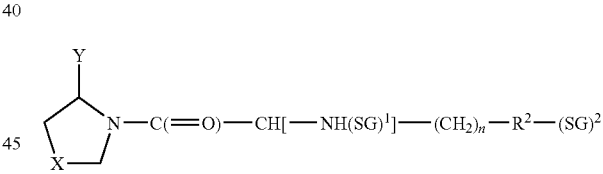

is transformed after cleavage of the protecting group $(SG)^2$ with a compound of the general formula

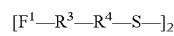

in which $R^3$ and $R^4$ might have the afore-mentioned general and specific meanings and $F^1$ is one part of the functional group which can react with one part of the other functional group; and the resulting reaction product is transformed releasing the protecting group $(SG)^1$ into a compound of a general formula A-B-D-B'-A' (1) in which A and A' might be identical or different and B and B' might be identical or different and in which A, A', B, B' and D might have the afore-mentioned meanings; in case of the following reaction scheme 2 A and A' are identical and are said X and Y containing heterocyclic compound with a carbonyl amino-group bound to a nitrogen atom; B and B' are also identical and are the group of the formula —$(CH_2)_n$—$R^2$— $R^3$— $R^4$— with the afore-mentioned general or specific meanings for n, $R^2$-$R^3$ and $R^4$ and D is —S—S—.

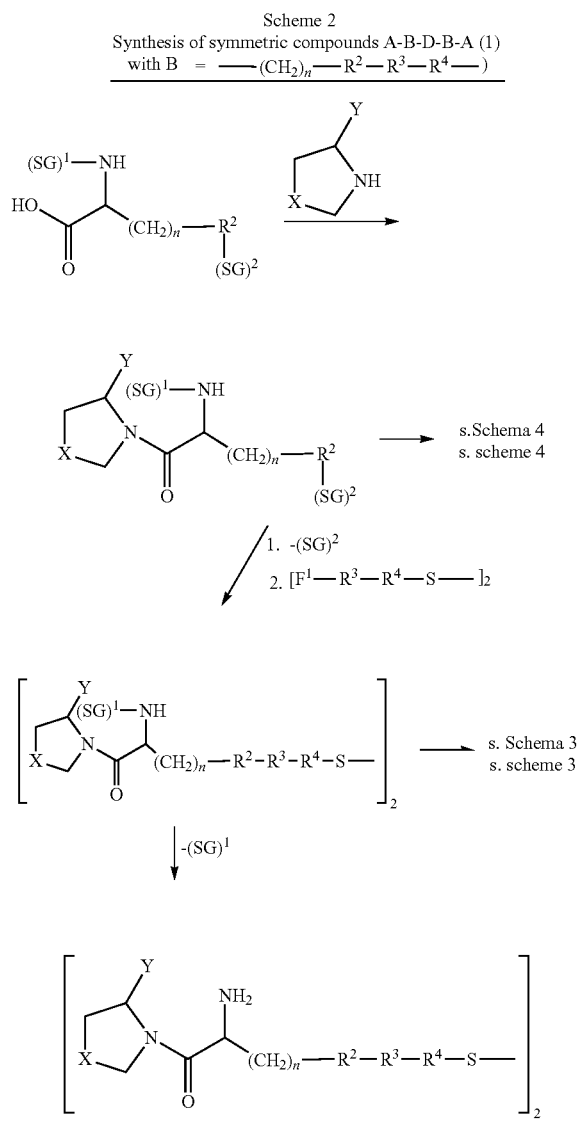

Scheme 2
Synthesis of symmetric compounds A-B-D-B-A (1)
with B = ——(CH$_2$)$_n$——R$^2$—R$^3$—R$^4$——)

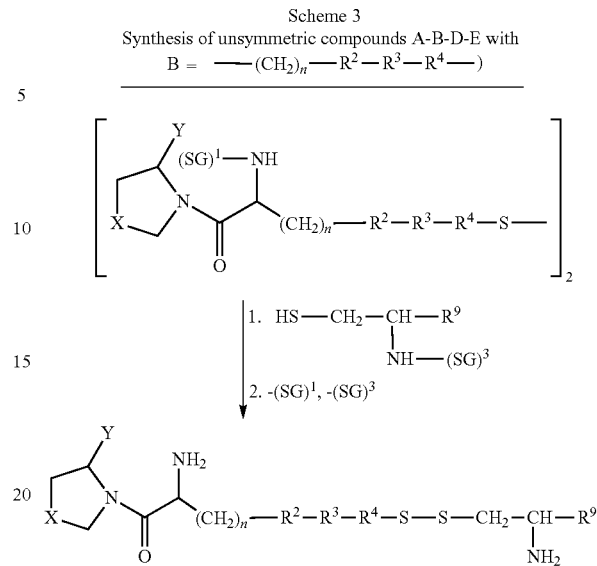

Scheme 3
Synthesis of unsymmetric compounds A-B-D-E with
B = ——(CH$_2$)$_n$——R$^2$—R$^3$—R$^4$——)

The protecting groups (SG)$^1$ and (SG)$^2$ are in general protecting groups as they are known by a person skilled in the field of organic synthesis for the intermediate protection of certain groups in organic molecules and are preferably urethane protecting groups, which are used for example as amino acid protecting groups. Not restricting examples are a benzyloxyl carbonyl-residue, a fluorene-9-ylmethoxylcarbonyl-residue or a tert-butyloxycarbonyl residue.

Using the first reaction steps of the preceding reaction scheme 2—starting from the dimer which results from the transformation with the compound of the formula [F$^1$—R$^3$—R$^4$— S—]$_2$— an unsymmetric compound of the formula A-B-D-E (2) can be obtained releasing the protecting group (SG)$^3$ while being transformed with a compound of the general formula HS—CH$_2$—CH(R$^9$)—NH(SG)$^3$ in which R$^9$ has the afore-mentioned general and specific meaning and (SG)$^3$ is a protecting group for the amino-group. This is shown in the following reaction scheme 3

In the unsymmetric compound obtained having the general formula A-B-D-E (2) A is the afore-mentioned X and Y containing heterocyclic compound with an α-aminocarbonyl-residue bound to the nitrogen; B is the group of the formula —(CH$_2$)$_n$—R$^2$—R$^3$— R$^4$— with the afore-mentioned general or specific meanings for n, R$^2$, R$^3$ and R$^4$, D is —S—S— and E is the group —CH$_2$—CH(NH$_2$)—R$^9$ in which R$^9$ has the afore-mentioned general and specific meanings.

In a second path of synthesis leading to unsymmetric compounds the residue B—starting from the first intermediate of the reaction scheme 2 shown above—is composed in subsequent reaction steps finally obtaining the same product like in the reaction of reaction scheme 3, as shown in the following reaction scheme 4:

The afore-mentioned first intermediate (see reaction scheme 2) is transformed being cleaved form the protecting group (SG)$^2$ into a compound with a suitable leaving group F$^2$ for the subsequent reaction with the compound of the general formulae F$^3$—R$^3$— R$^{4a}$-(SG)$^4$; in which F$^2$ and F$^3$ mean parts of functional (leaving-) groups. If R$^3$ has the afore-mentioned general and specific meaning R$^{4a}$ is a part of the group R$^4$ and (SG)$^4$ is a protecting group. The latter is transformed being cleaved into a suitable leaving group F$^4$. The transformation with a compound of the general formula F$^5$—R$^{4b}$—S—S—Z in which F$^5$ is a suitable functional leaving group, R$^{4b}$ is a second part of R$^4$ and Z is a residue which activates the molecule for a thiol exchange and the subsequent transformation with the thiol of the general formula HS—CH$_2$—CH (R$^9$)—NH(SG)$^3$ after cleaving the two protecting groups (SG)$^1$ and (SG)$^3$ lead to unsymmetric compounds of the general formula A-B-D-E (2) in which A is the afore-mentioned X and Y containing heterocyclic compound with an α-aminocarbonyl-residue bound to a nitrogen; B is the group of the formula —(CH$_2$)$_n$—R$^2$— R$^3$—R$^4$— with the afore-mentioned general or specific meanings for n, R$^2$, R$^3$ and R$^4$, D is —S—S— and E is the group —CH$_2$—CH(NH$_2$)—R$^9$ in which R$^9$ has the afore-mentioned general and specific meanings.

Scheme 4
Synthesis of unsymmetric compounds A-B-D-E
with B = ——(CH$_2$)$_n$——R$^2$—R$^3$—R$^4$——

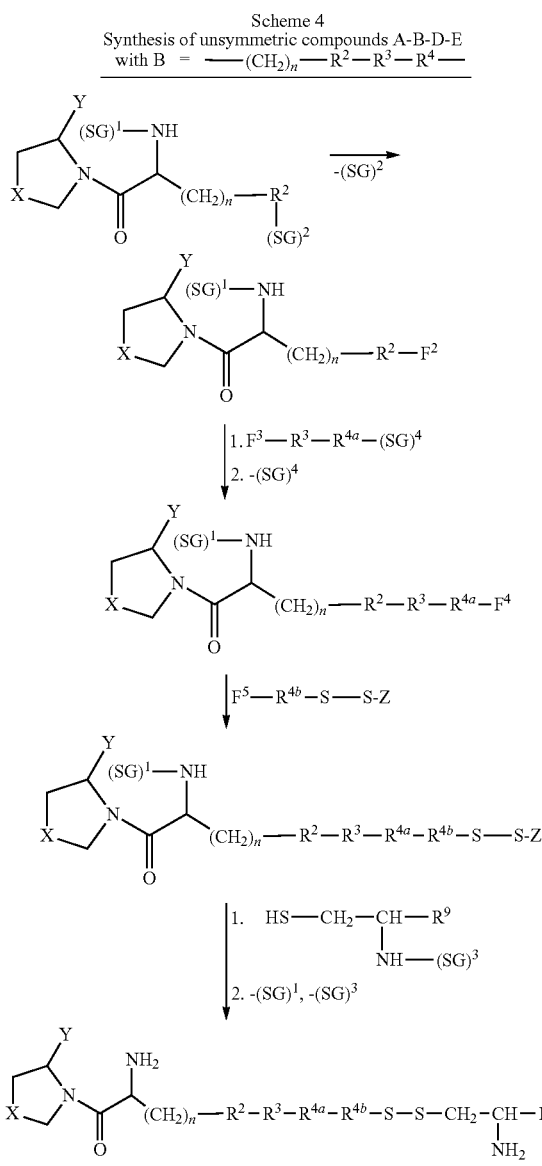

In the preceding reaction scheme 4 (SG)$^1$, (SG)$^2$, (SG)$^3$ and (SG)$^4$ are in general protecting groups as they are known to a person skilled in the field of organic chemistry for the intermediate protection of certain groups in organic molecules and are preferably urethane protecting groups which are usually used for example as amino acid protecting groups. Not restricting examples are a benzyloxylcarbonyl-residue, a fluorene-9-ylmethyloxycarbobyl-residue or a tert-butyloxycarbonyl-residue.

The residues F$^2$, F$^3$, F$^4$ and F$^5$ are parts of functional groups and designate leaving groups such as for example —H, —OH, —Cl etc. which are particularly suited to be cleaved from the molecule. Z are residues which activate a molecule containing an —S—S-group for a thiol exchange thus an exchange of a group for an S-atom (optionally attached to a substituent) of another molecule. Such groups are sufficiently known to a person skilled in the field of organic synthesis and the invention is not restricted to certain groups which activate for a thiol exchange. Preferred but not restricting examples are the groups 3-nitro-2-pyridyl, 5-nitro-2-pyridyl, 2-, 3- or 4-pyridyl, 2-nitrophenyl, methoxycarbonyl or N-methyl-N-phenylcarbamoyl. In the preceding scheme the residues R$^{4a}$ an R$^{4b}$ mean in combination the residue R$^4$ with the aforementioned general and specific meaning.

The starting compound of the following reaction scheme 5 in which R$^1$ has the meaning mentioned above in general and in detail can be transformed directly with the aforementioned heterocyclic compound of the general formula

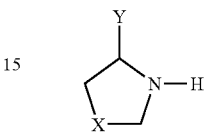

releasing the protecting group (SG)$^1$ into the symmetric compound of the general formula A-B-D-B'-A' (1) with B=R$^1$ in which X, Y and (SG)$^1$ have the afore-mentioned general and specific meanings:

Scheme 5
Synthesis of symmetric compounds
A-B-D-B-A (1) with B = R1)

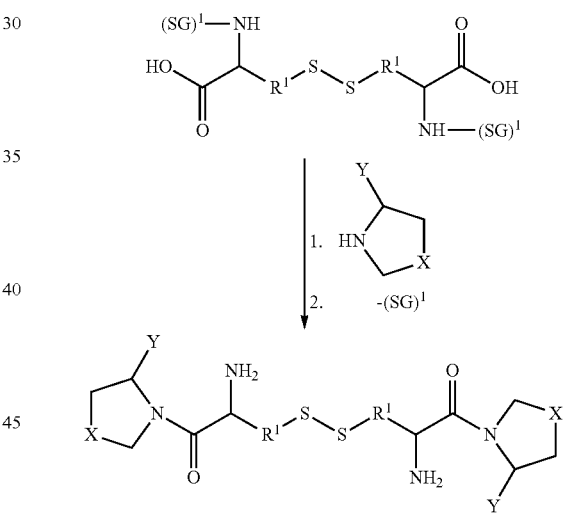

Using the preceding reaction path for example a final product is obtainable in which Y is CN by carrying out the aforementioned reaction with the heterocyclic compound

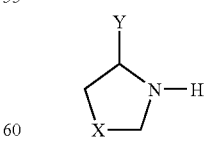

in which Y is —C(=O)—NH$_2$ and the symmetric reaction product in which Y is still —C(=O)—NH$_2$ is exposed to conditions under which the carbonyl amino group is transformed to a cyano-residue releasing water. This reaction results from the following reaction scheme 5a:

Scheme 5a
Synthesis of symmetric compounds A-B-D-B-A with Y = CN

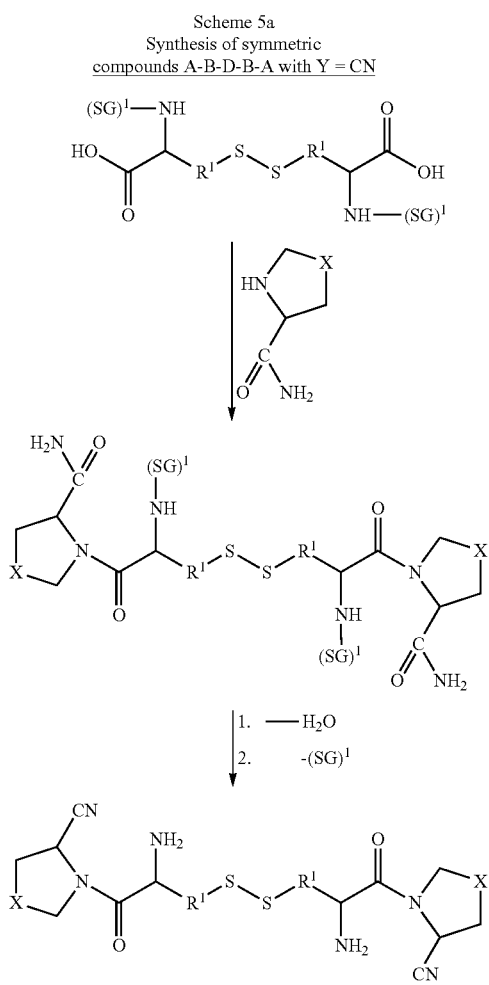

Unsymmetric compounds of the general formula A-B-D-E, in which B is $R^1$ and $R^1$ has the afore-mentioned general and specific meanings, are obtainable from the N-protected reaction product of reaction scheme 5 (see above) by transformation with a thiol compound of the general formula $HS-CH_2-CH[-NH(SG)^3]-R^9$ and cleavage of the protecting groups. This is shown in a reaction scheme 6:

Scheme 6
Synthesis of unsymmetric compounds A-B-D-E (2) with B = $R^1$

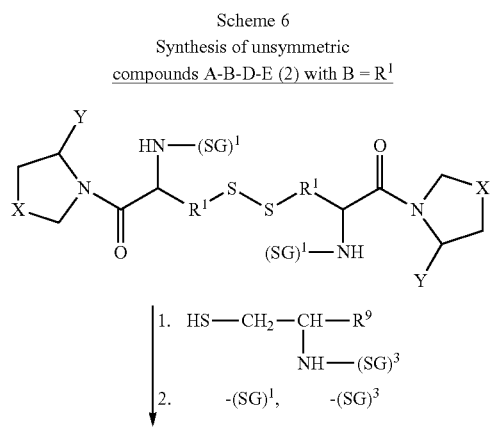

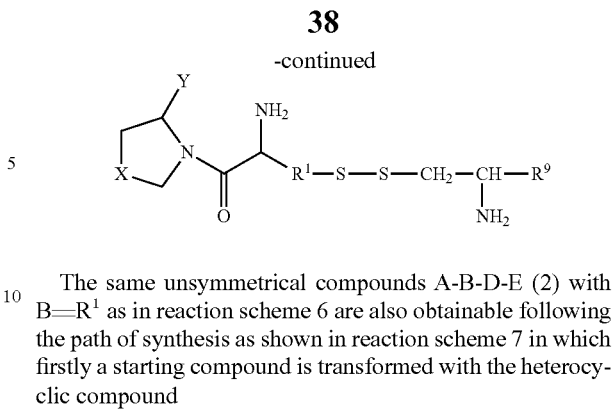

The same unsymmetrical compounds A-B-D-E (2) with $B=R^1$ as in reaction scheme 6 are also obtainable following the path of synthesis as shown in reaction scheme 7 in which firstly a starting compound is transformed with the heterocyclic compound The subsequent transformation with a thiol compound of the general formula $HS-CH_2-CH[-NH(SG)^3]-R^9$ and the cleavage of protecting groups $(SG)^1$ and $(SG)^3$ also leads to unsymmetrical compounds A-B-D-E (2) with $B=R^1$ in which $R^1$ may have the afore-mentioned general and specific meanings.

Scheme 7
Synthesis of unsymmetric compounds A-B-D-E (2) with B = $R^1$

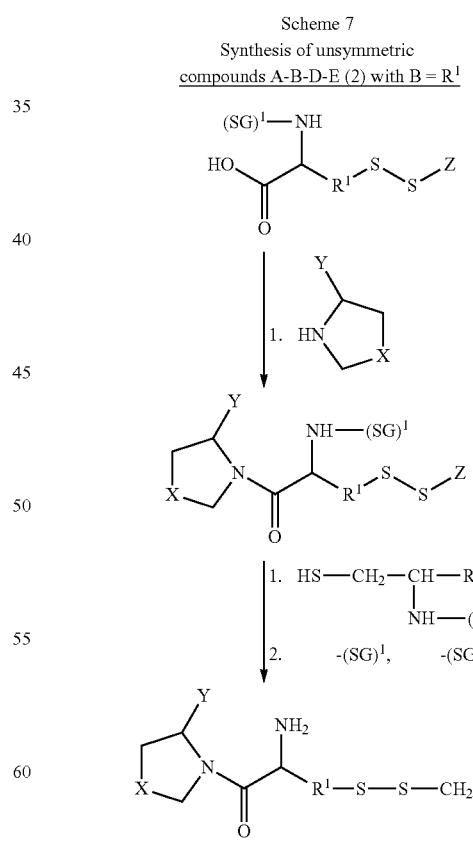

The following schemes of synthesis 8 and 9 show paths leading to the synthesis of symmetric compounds A-B-D-B-A (1) with $B=R^7-R^8-$ (scheme 8) and—starting from the N-protected product of the reaction of the scheme 8—to the synthesis of unsymmetric compounds A-B-D-E- (2) using paths of synthesis which are similar to the ones described above:

Scheme 8
Synthesis of symmetric compounds A-B-D-B-A (1)
with B = —R$^7$—R$^8$—)

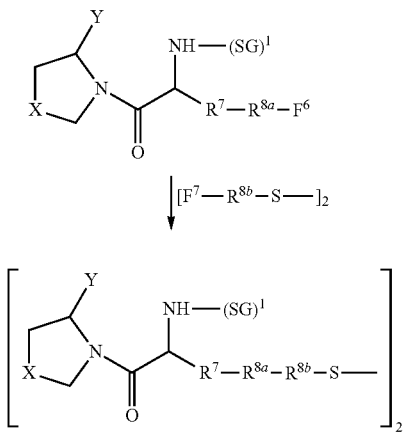

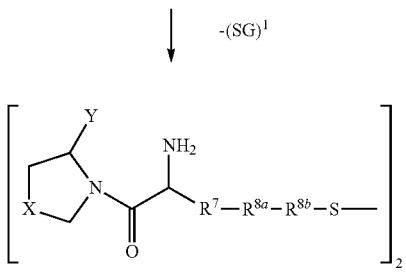

Scheme 9
Synthesis of unsymmetric compounds A-B-D-E (2)
with B = —R$^7$—R$^8$—

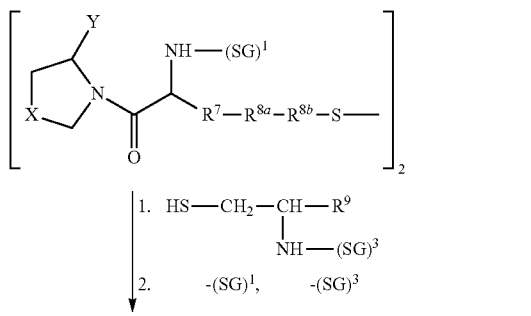

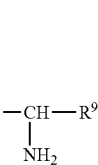

In the reaction schemes 8 and 9 the residues R$^{8a}$ and R$^{8b}$ are these residues which compose R$^8$ within two steps of the synthesis along said path.

Two further parts of synthesis which lead as well as the path of synthesis shown in reaction scheme 9 to unsymmetrical compounds A-B-D-E (2) with B=—R$^7$—R$^8$ and which are comparable to the reactions of synthesis as already shown above are presented in the following schemes of synthesis 10 and 11:

Scheme 10
Synthesis of unsymmetric compounds A-B-D-E (2) with B =
—R$^7$—R$^8$—

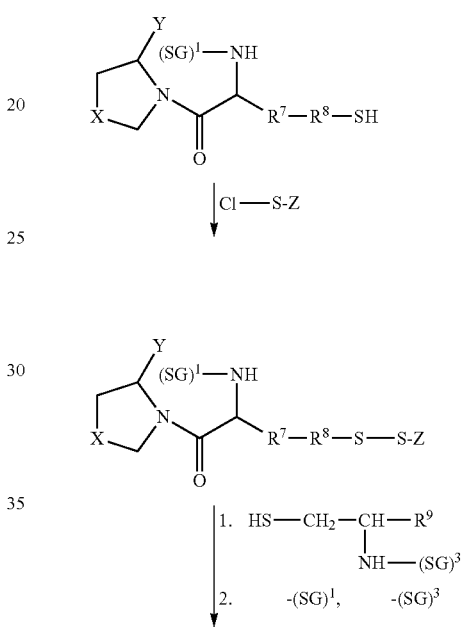

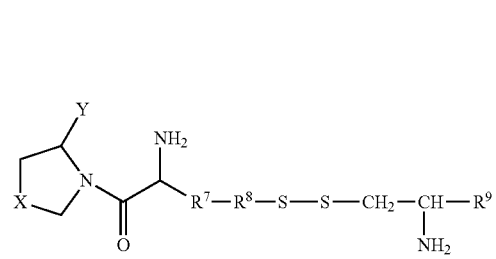

In all mentioned reaction schemes the residues F$^2$, F$^3$, F$^4$, F$^5$ and F$^6$ are parts of functional groups and designate leaving groups such as for example —H, —OH, —Cl etc. which are particularly suited to be cleaved from the molecule. Z are residues which activate the molecule containing an —S—S- group for a thiol exchange, hence an exchange of a group bound to the S-atom for an S-atom (optionally attached to a substitutent) of another molecule. Such groups are sufficiently known to a person skilled in the field of organic synthesis and the invention is not restricted to certain groups which activate for a thiol exchange. Preferred but not restricting examples are the groups 3-nitro-2-pyridyl, 5-nitro-2-pyridyl, 2-, 3- or 4-pyridyl, 2-nitrophenyl, methoxycarbonyl or N-methyl-N-phenylcarbamoyl. In the preceding scheme the residues $R^{4a}$ and $R^{4b}$ mean in combination the residue $R^4$ and the residues $R^{8a}$ and $R^{8b}$ mean in combination the residue $R^8$ both having the afore-mentioned general and specific meanings.

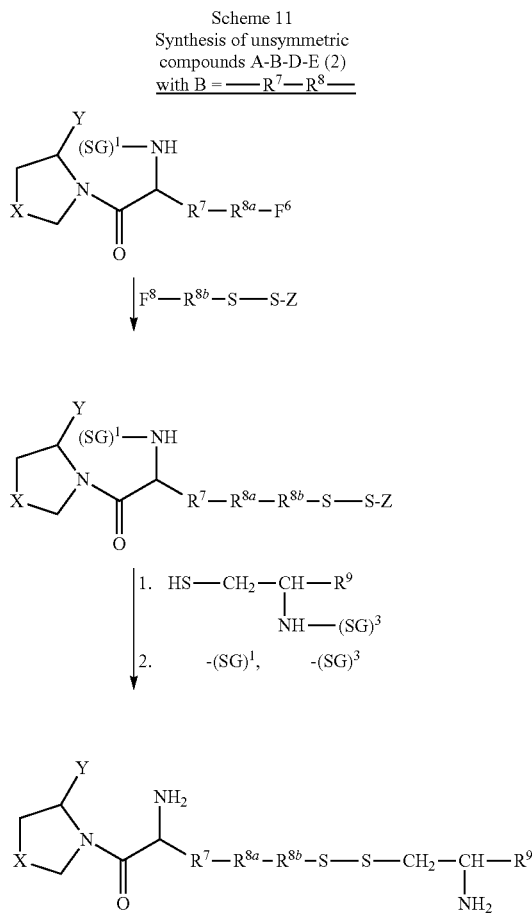

Scheme 11
Synthesis of unsymmetric compounds A-B-D-E (2) with B = —$R^7$—$R^8$—

The afore-mentioned and in the reaction schemes depicted reactions leading according to the invention to compounds of the general formulae (1) and (2) are carried out under conditions which are sufficiently known to a person skilled on the field of organic synthesis and do not require in this regard any further elaboration. Typical solvents used are polar organic solvents or mixtures of solvents. Particularly ethers are conceivable such as THF, esters such as acetic acid ethyl ester or DMF without restricting the invention hereunto. The temperature of reaction conforms with the transformation to be carried out and with the solvent used but lies usually in the range of −20° C. to +50° C. preferably in the range of 10° C. to 40° C.

According to the invention the compounds of the general formulae (1) and (2) accrue during their synthesis in form of acid addition salts according to one of the afore-mentioned processes particularly when their precise characterization and subsequent use in an aqueous milieu is to be carried out. Preferably acid addition salts with certain physiological (i.e. pharmacologically and/or cosmetically) acceptable inorganic or organic acids are prepared for the characterization and for the subsequent use of the compounds of the general formulae (1) and (2). In preferred embodiments of the invention salts of pharmaceutically acceptable acids from the group consisting of hydrochlorides, trifluoroacetates, tartrates, succinates, formiates and/or citrates of the compounds of the general formulae (1) or (2) are prepared as acid addition salts.

The compounds mentioned above in general and in detail (referring to formulae (1) and (2)) which can be prepared for example using one of the previously mentioned processes without restricting the preparation of the compounds to one of the said processes can be used for numerous purposes. Surprisingly it was found by the invention that the compounds can be used in the field of medicine. Particularly it was found that the new compounds according to the present invention themselves are inhibitors of the dipeptidyl peptidase IV or of enzymes with analogous enzymatic effect and of alanyl aminopeptidase N or of enzymes with analogous enzymatic effect.

In preferred embodiments of the invention the compounds can be successfully used as inhibitor precursors or inhibitor prodrugs. With regard to the definitions the terms "inhibitor", "precursor" and "prodrug" it can be referred to the afore-mentioned definitions.

Further preferred compounds according to the invention serve for the use as prodrugs for inhibitors of dipeptidyl peptidase IV (DPIV) and peptidases with analogous enzymatic effect as well as of alanyl aminopeptidases N (APN) and peptidases with analogous enzymatic effect. Even more preferred are compounds belonging to said compounds which serve for the use as prodrugs for inhibitors of dipeptidyl peptidase IV (DPIV) and alanyl aminopeptidase N (APN). Namely it was surprisingly found that compounds according to the invention can react under physiological or pathological conditions particularly under reducing conditions—as they are present in cells and tissues—to such compounds which are highly effective inhibitors of dipeptidyl peptidase IV (DPIV) and peptidases with analogous enzymatic effect, as well as for alanyl aminopeptidase N (APN) and peptidases with analogous enzymatic effect. According to the invention one of the new compounds according to formulae (1) or (2) mentioned above can be used according to the general or special description or more than one of the compounds mentioned above can be used in combination. Said combinations of more than one compounds can comprise either more than one compounds of the general formulae (1) or more than one compounds of the general formulae (2) or more than one compounds which are arbitrarily selected of the group of compounds of the general formulae (1) and (2) in combination. It is preferred to apply one compound of the general formulae (1) or (2) exclusively.

The invention also relates to the use of one or more compound(s) at least one compound particularly preferred exactly one compound of the general formulae (1) and/or (2) according to the afore-mentioned general and detailed description for the prophylaxis and therapy of diseases with exceeding immune response and inflammatory genesis, including arteriosclerosis, neuronal disease, cerebral damages, skin diseases, tumour diseases and virus-caused diseases as well as type II diabetes.

Furthermore the invention relates to the use of one or more compound(s), at least of one compound, particularly preferred exactly one compound of the general formulae (1) and/or (2) according to the afore-mentioned general and detailed description for the preparation of a medicament or a cosmetic preparation for the prophylaxis and therapy of diseases with exceeding immune response and inflammatory genesis including arteriosclerosis, neuronal diseases, cerebral damages, skin diseases, tumour diseases and virus-caused diseases as well as type II diabetes.

In preferred embodiments of the invention compounds of the general formulae (1) and/or (2) are used in general and preferably compounds according to the two afore-mentioned tables solely or the use in combination or in form of pharmaceutical or cosmetic preparations which comprise one or more of said compounds for the prophylaxis and therapy of diseases such as for example multiple sclerosis, Morbus Crohn, colitis ulcerosa, and other autoimmune diseases as well as inflammatory diseases, asthma bronchiale and other allergic diseases, skin- and mucosa-diseases, for example psoriasis, acne as well as dermatological diseases with hyper proliferation and modified conditions of differentiation of fibroblasts, benign fibrosing and sclerosing skin diseases and maligne fibroblastic conditions of hyper proliferation, acute neuronal diseases such as for example ischemia-caused cerebral damages after an ischemia—or haemorrhagic apoplexia, cranio-cerebral injury, cardiac arrest, heart attack or as a consequence of cardio surgical intervention, of chronic neuronal diseases for example of Morbus Alzheimer, of the Pick-disease, a progressive supra-nuclear palsy, the corticobasal degeneration, the frontotemporal dementia, of Morbus Parkinson, especially parkinsonism coupled to chromosome number 17, of Morbus Huntington, of prion-caused conditions of diseases and amyotrophic lateral sclerosis, of arteriosclerosis, arterial inflammation, stent-restenosis of chronic obstructive pulmonary disease (COPD), of tumours, metastases, of prostate carcinoma, of severe acute respiratory syndrome (SARS) and of sepsis and sepsis-like conditions as well as diabetes II.

In a further preferred embodiment of the invention the compounds of the general formulae (1) and/or (2) are used in general and preferably compounds according to the two afore-mentioned tables solely or the use in combination or in form of pharmaceutical or cosmetic preparations which comprise one or more of said compounds are used for the prophylaxis and therapy of the rejection of transplanted tissues and cells. As an example of such a use the use of one or more of the afore-mentioned compounds or of a pharmaceutical preparation containing one or more of the afore-mentioned compounds can be mentioned with regard to allogene or xenogene transplanted organs, tissues and cells such as kidney-, heart-, liver- pancreas-, skin- or stem cell transplantation as well as graft versus host diseases.

In a further preferred embodiment of the invention the compounds of the general formulae (1) and/or (2) in general and preferably the compounds according to the afore-mentioned tables are used solely or in combination or pharmaceutical or cosmetic preparations containing one or more of said compounds are used for the prophylaxis and therapy of reactions concerning rejection or inflammation at—or caused by—medical devices implanted into an organism. These can be for examples stents, joint implants (knee joint implants, hip joint implants), bone implants, cardio pace maker or other implants. In a further preferred embodiment of the invention the compounds of the general formulae (1) and/or (2) are used in general and preferably the compounds according to the afore-mentioned tables are used solely or in combination or pharmaceutical or cosmetic preparations are used containing one or more of said compound(s) in that way that the compound(s) or preparation(s) are applied in form of a coating or a wetting onto the item(s) or at least one of the compounds or preparations is materially admixed to the item(s). Also in this case it is certainly possible to apply one of the compounds or preparations—if applicable subsequently or parallelly—locally or systemically.

In the same way as mentioned above—and for comparable purposes or for prophylaxis and therapy of the above exemplary but not completely mentioned diseases and conditions—the compounds of the general formulae (1) and (2) in general and the compounds according to the two afore-mentioned tables in preferred embodiments as well as the following pharmaceutical and cosmetic preparations containing said compounds can be used solely or in combination of more than one of them to prepare medicaments for the treatment of the afore-mentioned diseases and conditions. These can comprise the afore-mentioned compounds in amounts mentioned in the following, optionally in combination with per se known carrier substances auxiliary substances and/or additives.

In preferred embodiments the use of the compounds of the afore-mentioned general formulae (1) and/or (2) comprises such cases in which the used compound(s) generate(s) at least one inhibitor of dipeptidyl peptidase IV (DPIV) and peptidases with analogous enzymatic effect as well as alanyl aminopeptidase N (APN) and peptidases with analogous enzymatic effect. The generation of at least one of such inhibitors preferably two or more than two of such inhibitors particularly preferred one or two inhibitors from a compound leads to a surprising specificity of the use according to the invention in the medical fields particularly as inhibitors of one or more enzymes of the afore-mentioned groups.

In a further preferred embodiment the use of one or more compounds of the afore-mentioned formulae (1) and/or (2) or of cosmetic or pharmaceutical preparations comprising at least one of the compounds of the general formulae (1) and/or (2) leads to at least one inhibitor preferably to one inhibitor or two inhibitors of enzymes of the group mentioned above if reducing conditions are present particularly if reducing conditions are present at a position at which the resulting compound(s) which is/are formed develop(s) its/their pharmacological effect.

Using the term "reducing conditions" in this context conditions of a chemical reaction are recognized in which the compound(s) of the general formula (1) or the compound(s) of the general formula (2) or one or more compound(s) of the general formulae (1) and (2) in combination are exposed to reaction conditions at the site of an effect in which an electron-donor supplies electrons for the acceptance by the compound(s) of the general formulae (1) and/or (2). As it was found according to the invention compounds of the general formulae (1) and/or (2) are transformed under reducing conditions cleaving an —S—S- or —Se—Se-bridge designated by D in the general formulae (1) and (2) into two compounds with an —SH-terminal group or an —SeH-terminal group, respectively.

It is for the invention without any crucial importance by which means the reducing physiological reaction conditions are achieved as long as they achieve a reliable generation of the accordant molecules with an —SH- or an —Se-terminating group. The compounds according to the invention regularly meet the conditions which lead to the in-vivo generation of suitable compounds being inhibitors of the afore-mentioned enzymes.

The amounts of at least one of the compounds of the general formulae (1) and/or (2) in general or of the afore-mentioned compounds accordant to the two preceding tables are in the scope of the inventive use in the range of 0.01 to 1000 mg with regard to at least one of the compounds of the general formulae (1) and/or (2) per application unit preferably in the range of 0.1 to 100 mg per application unit.

In the context of the inventive use an application of at least one, of said compounds of general formulae (1) and/or (2) can be achieved on any pathway per se known which a person normally skilled in this technical field knows. The application of compounds of the general formulae (1) and/or (2) in general and further preferred the compound according to the afore-mentioned tables or pharmaceutical or cosmetic preparations, respectively, which comprise one or more of the afore-mentioned compounds in combination with per se known usual carrier substances, auxiliary substances and/or additives is either carried out as topic application in form of for example crèmes, salves, pastes, gels, solutions, sprays, liposomes and nanosomes, shake mixtures, "pegylated" formulations degradable (e.g. under physiological conditions degradable) depot-matrices, hydrocolloid-bandages, plasters, micro-sponges, prepolymers and similar new carrier substrates, jet-injection or other dermatological principles/vehicles including instillative application and on the other hand as systemic application for oral, transdermal, intravenous, subcutane, intracutane, intramuscular, intrathecal application in suitable formulations or suitable galenic, thus in form of tablets, dragees, lozenges, capsules, aerosols, sprays, solutions, emulsions and suspensions.

The invention also relates to a process for the inhibition of the alanyl aminopeptidase N activity or of the activity of peptidases with analogous enzymatic effect as well as the dipeptidyl peptidase IV activity or of the activity of peptidases with analogous enzymatic effect either solely or in combination with other inhibitors of alanyl aminopeptidase N or inhibitors of peptidases with analogous enzymatic effect and/or other inhibitors of DPIV or inhibitors of peptidases with analogous enzymatic effect by the application of at least one compound of the general formulae (1) and/or (2) or a pharmaceutical or cosmetic preparation which comprises at least one of the compounds of the general formulae (1) and/or (2) according to the afore-mentioned detailed description in an amount necessary for the inhibition for the enzyme activity. The amounts of the compounds of the general formulae (1) and/or (2) in general or the compounds according to the two afore-mentioned tables, respectively, are in the range—as mentioned above—of 0.01 to 1000 mg of at least one compound per application unit, preferably in the range of 0.1 to 100 mg per application unit.

Further the invention relates to a process for the topic influence of the alanyl aminopeptidase N activity or of the activity of peptidases with analogous enzymatic effect as well as of the activity dipeptidyl peptidase IV or of the activity of peptidases with analogous enzymatic effect either solely or in combination with other alanyl aminopeptidase N inhibitors or inhibitors of peptidases with analogous enzymatic effect and for other DPIV inhibitors or inhibitors of peptidases with analogous enzymatic effect by the application of at least one compound of the general formulae (1) and/or (2) or of pharmaceutical or cosmetic preparations according to the following detailed description in an amount necessary for the manipulation of the enzyme activity. Also in these cases the amounts of the compound(s) of the general formulae (1) and/or (2) are in the range mentioned above.

Furthermore the invention relates to a process for to generate at least one inhibitor of dipeptidyl peptidase IV (DPIV) and peptidases with analogous enzymatic effect as well as alanyl aminopeptidase N (APN) and peptidases with analogous enzymatic effect from at least one of the compounds of the general formulae (1) and (2). The process according to the invention comprises the step that at least one of the compounds of the general formulae (1) and (2) is exposed to reducing conditions according to the afore-mentioned description. As previously described a skilled person is not restricted with regard to reducing conditions for the transformation of at least one compound of the general formulae (1) and/or (2) which can insofar as well be regarded as intermediate in the synthesis of inhibitors according to the invention of dipeptidyl peptidase IV (DPIV) and inhibitors of peptidases with analogous enzymatic effect as well as inhibitors of the alanyl aminopeptidase N (APN) and inhibitors of peptidases with analogous enzymatic effect into the actual inhibitors of a dipeptidyl peptidase IV (DPIV) and inhibitors of peptidases with analogous enzymatic effect as well as inhibitors of alanyl aminopeptidase N (APN) and inhibitors of peptidases with analogous enzymatic effect.

Furthermore the invention relates to a process for the prophylaxis and therapy of numerous diseases, for example diseases with exceeding immune response (autoimmune diseases, allergies and transplant rejections) of other chronic inflammatory diseases, neuronal diseases and cerebral damages, skin diseases (inter alia acne and psoriasis), tumour diseases and particular virus infections (inter alia SARS) as well as type II diabetes and particularly the diseases mentioned above in detail. This includes: processes for the prophylaxis and therapy of diseases such as for example multiple sclerosis, Morbus Crohn, colitis ulcerosa, and other autoimmune diseases as well as inflammatory diseases, asthma bronchiale and other allergic diseases, skin- and mucosa diseases for example psoriasis, acne as well as dermatological diseases with hyperproliferation and modified conditions of differentiation of fibroblasts, benign fibrosing and sclerosing skin diseases and malign fibroblastic hyper proliferation conditions, acute neuronal diseases, such as for example ischemia-caused cerebral damages after an ischemia- or haemorrhagic apoplexia, cranio-cerebral injury, cardiac arrest, heart attack or as a consequence of cardio-surgical interventions, of chronic neuronal diseases such as for example Morbus Alzheimer, the Pick-disease, the progressive supra-nuclear palsy, the corticobasal denegeration, the frontotemporal dementia, of Morbus Parkinson, particularly parkinsonism coupled to chromosome 17, of Morbus Huntington, or disease conditions caused by prions and of amyotrophic lateral sclerosis, of arteriosclerosis, arterial inflammations, stent-restenosis, of chronic obstructive pulmonary diseases (COPD), of tumours, metastases, of prostate carcinoma, of severe acute respiratory syndrome (SARS) and of sepsis and sepsis-like conditions. The process comprises an application of at least one compound or pharmaceutical preparation according to the following detailed description in an amount necessary for the prophylaxis or therapy of the accordant disease. Also in these cases the amounts of compound(s) is/are in the afore-mentioned range of 0.01 to 1000 mg of a compound per application unit preferably in a range of 0.1 to 100 mg per application unit.

The invention also relates to pharmaceutical preparations which comprise at least one compound of at least one of the general formulae (1) and (2) of the afore-mentioned general and detailed description optionally in combination with one or more pharmaceutically acceptable carrier substance(s), auxiliary substance(s) and/or adjuvant(s).

Furthermore the invention also relates to cosmetic preparations which comprise at least one of the compounds of at least one of the general formulae (1) and (2) of the afore-mentioned general and detailed description if applicable in combination with one or more cosmetically acceptable carrier substance(s), auxiliary substance(s) and/or adjuvant(s).

With regard to these preparations the pharmaceutically or cosmetically acceptable carrier substances, auxiliary substances and/or adjuvants are sufficiently known to a person skilled in the pharmaceutical or cosmetic field and do not require any further detailed mentioning.

The mentioned pharmaceutical or cosmetic preparations, might contain at least one compound of the general formulae (1) or (2), preferably one or two compounds of the general formulae (1) and/or (2) in such amount(s) which is/are necessary for the desired effect in the pharmaceutical or cosmetic field. The amount(s) is/are not particularly restricted and is/are dependent on a number of parameters such as for example the application pathway, the specific disease pattern or the cosmetic status, of the constitution of the addressee who can be a mammal such as for example a human, of the bio-availability of the used compound(s) etc. In particularly preferred embodiments a pharmaceutical application unit or a cosmetic application unit, respectively, contains an amount of at least one compound of the general formula (1) and/or (2) which is in the range of 0.01 to 1000 mg of a compound per application unit, preferably in the range of 0.1 to 100 mg per application unit. Usually the application units can be of that ilk (and contain such concentrations of at least one compound of the general formulae (1) and/or (2)) that the application of one or less further preferred two or three application units per day is sufficient to apply an amount necessary for a systematic pharmaceutical or cosmetic treatment with regard to at least one of the compounds (1) and/or (2) to the patient such as for example a mammal, particularly a human.

The invention is explained in the following by examples of particularly preferred embodiments. The following examples of embodiments are not to restrict the invention but only to give an exemplary illustration.

EXAMPLES

Example 1

Preparation of Compounds of the General Formula (1)

Compounds of the general formula (1) were prepared using the following process:
(a) Compound II (Scheme 12)

440 mg (1 mmol) (Boc-Cys-OH)$_2$ 1 were dissolved in 5 ml dry THF. Under argon 158 µl (2 mmol) thiazolidine were added to the solution and after 25 min at 0° C. gradually 460 mg (2.4 mmol) N'-(3-dimethylaminopropyl)-N-ethylcarbodiimid (EDC) were added. The transformation was controlled at RT by means of thin layer chromatography (TLC). After 6 h a further activation was carried out using 460 mg (2.4 mmol) EDC and 79 µl (I mmol) thiazolidine at 0° C. After 20 h the THF was removed by distillation and the solid residue was dissolved in ethylacetate. The ethylacetate phase was rinsed 3 times with 5% KHSO$_4$-solution, once with NaCl-solution, 3 times with saturated NaHCO$_3$-solution and 3 times with NaCl-solution. It was dried above Na$_2$SO$_4$, filtrated and concentrated.

The obtained raw product was purified by crystallisation from a mixture of ethylacetate/petrolether.

468 mg (80%) of the accordant Boc-protected compound were obtained. In order to cleave the protecting groups 468 mg (0.8 mmol) of this compound were dissolved in 1.2 ml (16 mmol) trifluoroacetic acid and 12 ml methylenechloride. The reaction was controlled by means of TLC and dry ether was added to the reaction batch after the transformation was completed. The precipitating solid was filtered and rinsed several times with ether.

Yield: 446 mg (91%) II.

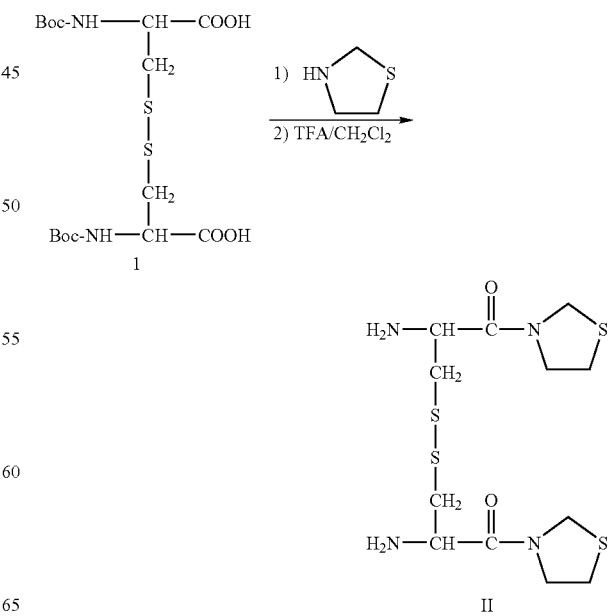

(b) Compound VI (scheme 13)

(i) Boc-Lys-thiazolidide 3

1.4 g (3 mmol) Boc-Lys(Fmoc)-OH 2 and 382 µl (3 mmol) 4-ethylmorpholin were dissolved in 7 ml dry THF. The reaction batch was cooled to −15° C. and at this temperature 390 µl (3 mmol) chloroformic acid isobutyl ester were added. After a reaction time of 15 minutes at −15° C. 284 µl (3.6 mmol) thiazolidine were added, the batch was agitated for another hour at −15° C. and subsequently over night at RT.

To complete the transformation half of the afore-mentioned amounts were again activated cooling the batch to −15° C. after the addition of 4-ethlymorpholine and chloroformic acid isobutyl ester and thiazolidine were added as described. After another 4 hours of reaction time at RT it was concentrated until completely dried and the residue was dissolved in ethylacetate.

The ethylacetate phase was rinsed 3 times with 5% $KHSO_4$-solution, once with NaCl-solution, 3 times with saturated $NaHCO_3$-solution and subsequently with NaCl-solution until neutral.

After drying above $Na_2SO_4$ the ethylacetate phase was concentrated and the residue was dissolved in 30 ml morpholine to cleave the Fmoc-protecting group.

After 1.5 h of reaction time at RT the morpholine was removed by distillation. 6 ml ice-cold methanol were added to the residue. The solution was filtered from hardly soluble 4-fluoroene-9-ylmethylmorpholine and the solution was concentrated.

Yield: 875 mg (92%) 3

(ii) Synthesis of VI

To the solution of 181 mg (0.5 mmol) 4 in 3 ml DMF gradually 240 mg (1.25 mmol) EDC were added at 0° C. and subsequently 317 mg (1 mmol) 3 were added.

The reaction batch was agitated for 1 h at 0° C. and subsequently 6 h at RT. After the addition of another 120 mg (0.63 mmol) EDC and 6 hours of incubation time the DMF was removed by distillation and the residue was dissolved in ethylacetate. The ethylacetate phase was washed 3 times with 5% $KHSO_4$-solution, once with NaCl-solution, 3 times with saturated $NaHCO_3$-solution and subsequently with NaCl-solution until neutral.

After drying above $Na_2SO_4$ and removal of the ethylacetate by distillation 440 mg of the raw product remained.

Using chromatographic purification on silica gel with the eluent chloroform/methanol 92/8 the yield obtained was 250 mg (55%) 8.

In order to the protecting groups 20 mg (0.022 mmol) 8 were dissolved in 220 µl 1 M HCl in pure acetic acid. After standing for 6 hours at RT dry ether was added to the reaction batch and the precipitating product was filtered and rinsed with ether.

Yield: 15 mg (88%) VI

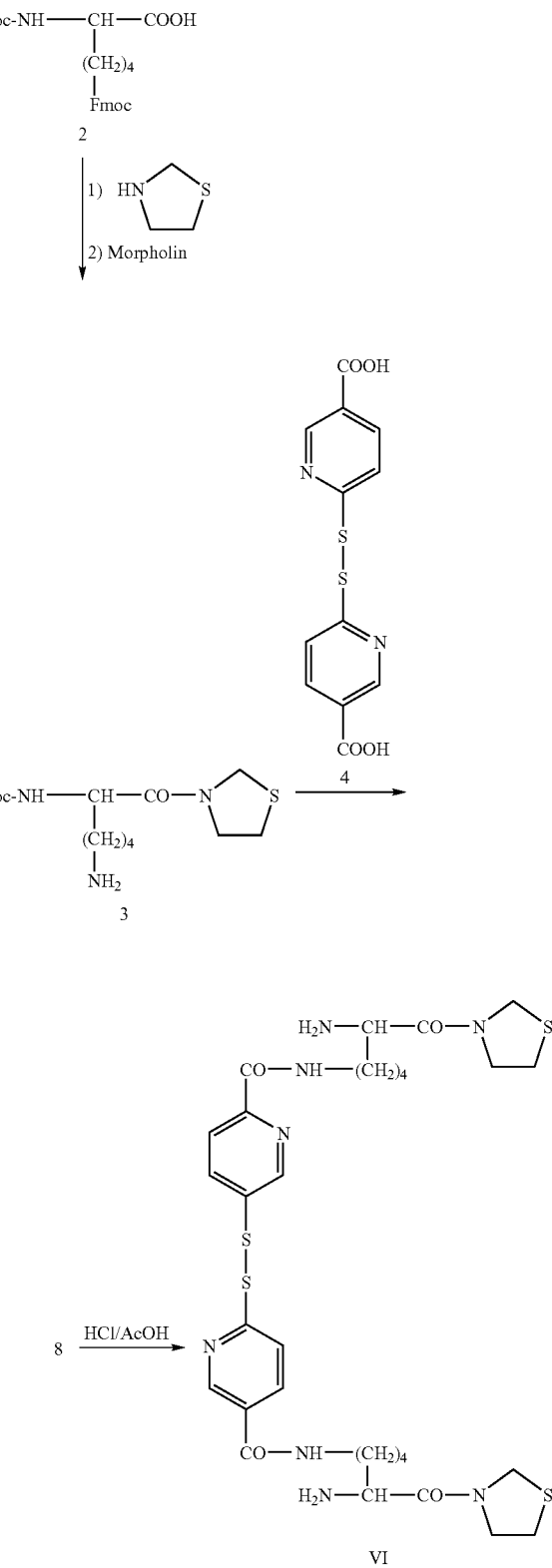

Scheme 13

The compounds obtained were characterised by ESI-MS. The following table 3 presents 6 examples of compounds of the general formula (1) according to the invention

TABLE 3

Examples for compounds of the general formulae A-B-D-B'-A' (1)

[Structure: pyrrolidine-N-C(O)-CH(NH2)-B-S-S-B-CH(NH2)-C(O)-N-pyrrolidine with X and Y substituents on the rings]

| No. | B | X | Y | Empirical formula | Molar weight | ESI-MS [m/e] |
|---|---|---|---|---|---|---|
| I | —CH₂— | —CH₂— | H | $C_{14}H_{26}N_4O_2S_2$ | 346.5 | 347.2 |
| II | —CH₂— | S | H | $C_{12}H_{22}N_4O_2S_4$ | 382.6 | 383.0 |
| III | —CH₂— | —CH₂— | CN | $C_{16}H_{24}N_6O_2S_2$ | 396.5 | 397.1 |
| IV | —(CH₂)₄—NH—C(=O)—CH(NH₂)—CH₂— | S | H | $C_{24}H_{46}N_8O_4S_4$ | 638.9 | 639.2 |
| V | —(CH₂)₄—NH—C(=O)—(2-NO₂-4-methylphenyl) | S | H | $C_{32}H_{42}N_8O_8S_4$ | 795.0 | 795.2 |
| VI | —(CH₂)₄—NH—C(=O)—(methylpyridyl) | S | H | $C_{30}H_{42}N_8O_4S_4$ | 707.0 | 707.2 |

Example 2

Preparation of Compounds of the General Formula (2)

Compounds of the general formula (2) were prepared using the following process:

(a) Compound VII (scheme 14)

(i) Synthesis of 6

188 mg (0.5 mmol) Boc-Cys(Npys)-OH 5 were dissolved in 2.5 ml dry THF. Under argon 40 µl (0.5 mmol) thiazolidine and gradually 115 mg (0.6 mmol) EDC were added at 0° C. The reaction was tracked at RT by means of TLC and terminated after 4 h. For this purpose the reaction batch was concentrated, the solid residue was dissolved in ethylacetate and the organic phase was rinsed subsequently 3 times with 5% KHSO₄-solution, once with NaCl-solution, 3 times with saturated NaHCO₃-solution and 3 times with NaCl-solution. After drying above Na₂SO₄ it was filtrated and the ethylacecate phase was concentrated.

Yield: 191 mg (86%) 6

(ii) Synthesis of VII 29 mg (0.065 mmol) 6 were dissolved in 5 ml ACN/phosphate buffer (1:1), pH 8.0. To this solution a solution of 18 mg (0.065 mmol) β-aminothiol 7 (synthesized in three steps starting from (S)-phenylalaminol according the "Fournier-Zaluski, M. C.; Coric, P.; Turcaud, S.; Bruetschy, L., Lucas, E.; Noble, F.; Roques, B. P. J. Med. Chem. 1992, 35, 1259-1266"; "Fournier-Zaluski, M. C.; Coric, P.; Turcaud, S.; Lucas, E.; Noble, F.; Maldonado R.; Roques, B. P. J. Med. Chem. 1992, 35, 2473-2481") in 5 ml ACN/phosphate buffer was added under argon at RT. After a reaction time of 3 h (HPLC-control) the reaction was terminated by concentrating the reaction batch, dissolving the solid residue in ethylacetate and by rinsing this phase 3 times with NaCl-solution. It was dried above Na₂SO₄, filtrated and concentrated. The obtained raw product was chromatographically purified on silica gel with ethylacetate/petrolether. The yield was 20 mg (55%) of the accordant Boc-protected compound. In order to cleave the protecting groups 10 mg (0.018 mmol) of this compound was dissolved in 28 µl (0.36 mmol) trifluoroacetic acid and 280 µl methylenechloride. The reaction was tracked by means of TLC and terminated by adding dry ether to the reaction batch. The precipitating product was rinsed several times with ether.

Yield: 8 mg (76%) VII.

Scheme 14

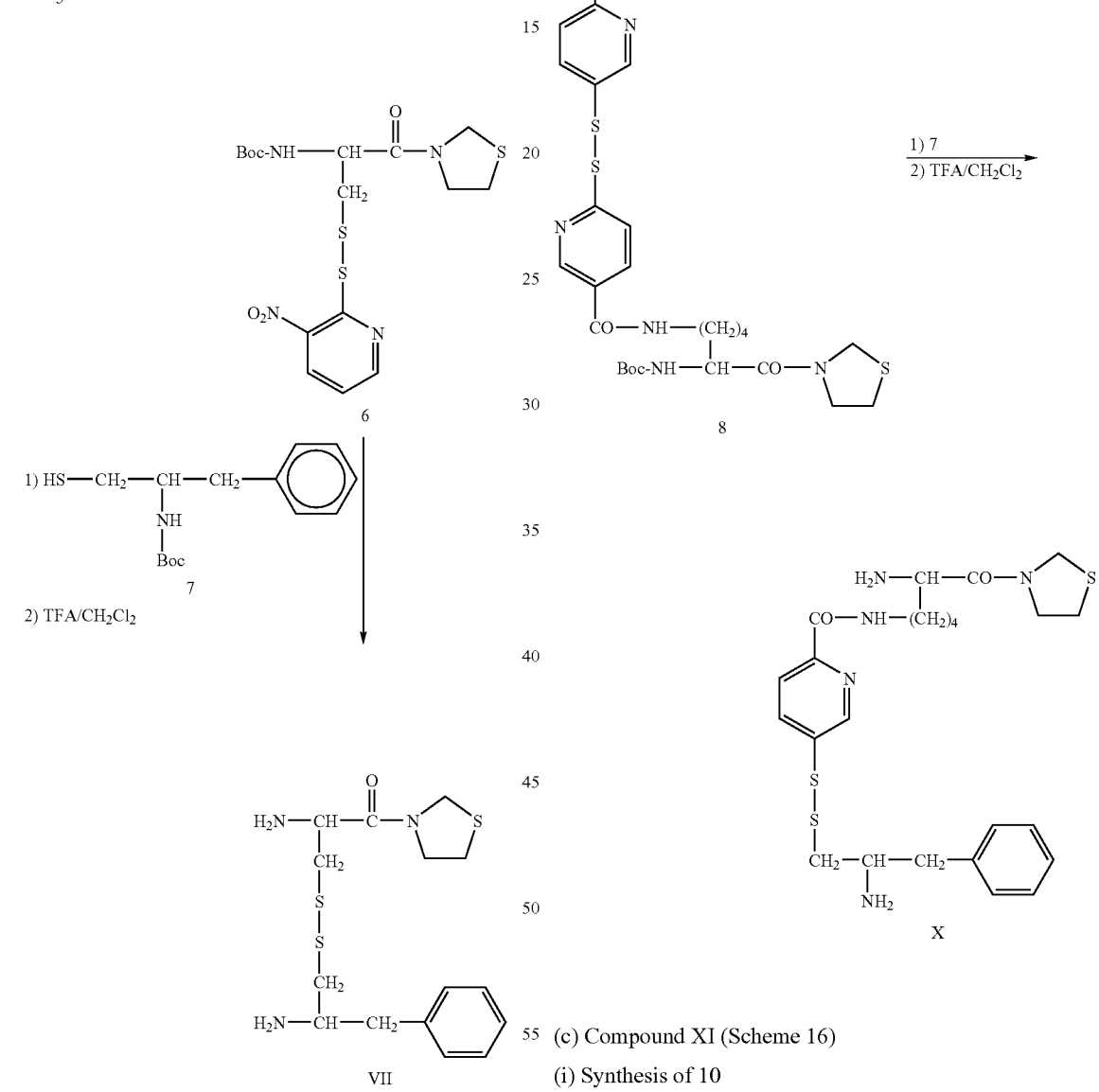

(b) Compound X (Scheme 15)

73 mg (0.08 mmol) 8 and 20 mg (0.075 mmol) β-aminothiol 7 were agitated in 3 ml methanol for 24 hours at RT. After the removal of the methanol by distillation the raw product was purified on silica gel with the eluent ethylacetate/petrolether 95/5. The yield was 34 mg Boc-protected disulfide (63%) which was dissolved in order to cleave the protecting group in 750 µl methylenechloride and 75 µl trifluoroacetic acid were added. After standing for 6 hours at RT dry ether was added and the precipitating product was filtered and rinsed with ether. Yield: 29 mg (83%) X.

(c) Compound XI (Scheme 16)

(i) Synthesis of 10

190 mg (0.5 mmol) 3-(Fmoc-aminomethyl)-benzoe acid 9 and 64 µl (0.05 mmol) 4-ethylmorpholine were dissolved in 1 ml DMF and cooled under argon to −15° C. To this solution 65 µl (0.5 mmol) chloroformic acid isobutyl ester was added, the solution was agitated for 20 min at −15° C. and subsequently a solution of 159 mg (0.5 mmol) Boc-Lys-thiazolidide 3 in 1.25 ml DMF was added and the solution was agitated for 1 h at −15° C.

After 20 h at RT 32 µl (0.25 mmol) 4-ethyl-morpholine and 33 µl (0.25 mmol) chloroformic acid isobutyl ester were again added at −15° C. for another activation.

The DMF was distilled after 40 h (TLC-control) and dissolved in ethylacetate. The ethylacetate phase was rinsed 3 times with 5% KHSO₄-solution, once with NaCl-solution, 3 times with saturated NaHCO₃-solution, once with NaCl-solution, 3 times with saturated NaHCO₃-solution and 3 times with NaCl-solution. It was dried above Na₂SO₄, filtered and subsequently concentrated. The obtained raw product was purified chromatographically on silica gel with ethylacetate.

The yield was 174 mg (52%) of the according Fmoc-protected compound. In order to cleave the protecting groups 150 mg (0.22 mmol) of this compound was dissolved in 2.2 ml morpholine and after 2 h the excessive morpholine was removed by distillation. The residue was dissolved in 1 ml ice-cold methanol, filtrated from the insoluble 4-fluorene-9-ylmethylmorpholine and concentrated.

Yield: 92 mg (93%) 10

(ii) Synthesis of 11

78 mg (0.21 mmol) Boc-Cys(Npys)-OH 5 and 27 µl (0.21 mmol) 4-ethyl-morpholine were dissolved in 0.4 ml THF and cooled under argon to −15° C. To this solution 28 µl (0.21 mmol) chloroformic acid isobutyl ester were added, it was agitated for 20 min at −15° C. at subsequently a solution of 95 mg (0.21 mmol) 10 in 0.75 ml THF were added. After 1 h at −15° C. and 20 h at RT 13 µl 4-ethylmorpholine (0.10 mmol) and 13 µl (0.10 mmol) chloroformic acid isobutyl ester were added at −15° C. for another activation step.

The THF was removed after 24 h (TLC-control) by distillation and the reaction batch was processed as in case of compound 10.

The obtained raw product was subsequently purified chromatographically on silica gel with methanol/chloroform. Yield: 100 mg (60%) 11.

(iii) Synthesis of XI 67 mg (0.08 mmol) 11 were dissolved in 8 mg acetonitrile/phosphate buffer (1:1), pH 8.0. A solution of 21 mg (0.08 mmol) 7 in 8 ml acetonitrile/phosphate buffer was added under argon at RT. The reaction was tracked by means of HPLC and the reaction batch was concentrated after terminated reaction. The solid residue was dissolved in ethylacetate and rinsed 3 times with NaCl-solution, dried above Na₂SO₄, filtered and concentrated. The raw product was subsequently purified chromatographically on silica gel with ethylacetate/petrolether. The yield was 29 mg (40%) of the according Boc-protected compound. In order to cleave the protecting group 22 mg (0.024 mmol) of this compound were dissolved in 55 µl trifluoroacetic acid and 550 µl methylenechloride. The reaction was checked by means of TLC and ether was added to the reaction batch after the termination of the cleavage. The precipitated product was filtered and rinsed several times with ether. Yield: 16 mg (70%) XI.

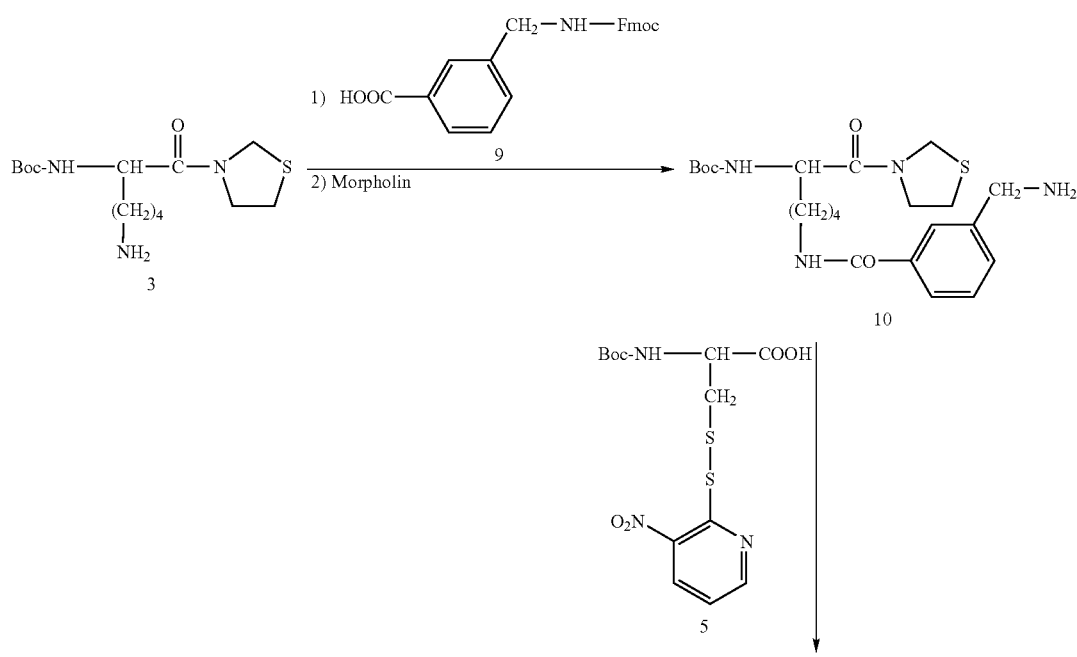

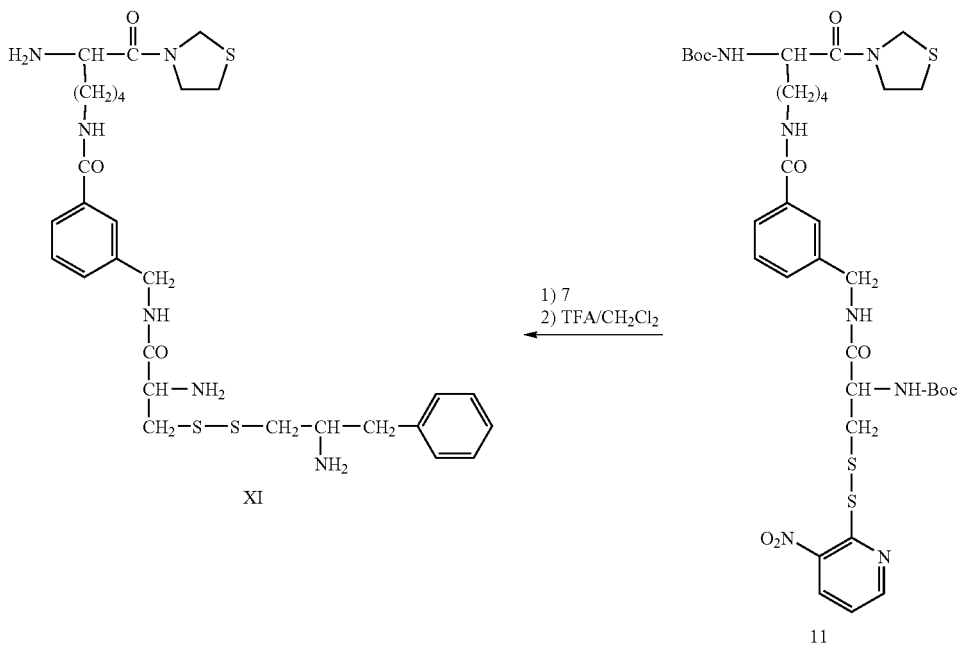

(d) Compound XIII (Scheme 17)

(i) Synthesis of 13

2.5 g (5 mmol) Boc-p-Amino-Phe(Fmoc)-OH 12 were dissolved in 25 ml dry THF. Under argon 394 µl (5 mmol) thiazolidine were added at 0° C. and gradually 1.15 g (6 mmol) EDC. The reaction was checked by means of TLC at RT. After 6 h 197 µl (2.5 mmol) thiazolidine and 954 mg (5 mmol) EDC were added at 0° C. for another activation step. The reaction was terminated after another 2 h at RT by concentrating the reaction batch dissolving the solid residue in ethylacetate and by rinsing the organic phase 3 times with 5% $KHSO_4$-solution, once with NaCl-solution, 3 times with saturated $NaHCO_3$-solution, 3 times with NaCl-solution. Subsequently it was dried above $Na_2SO_4$, filtered and concentrated.

The yield was 2.58 g (90%) of the corresponding Fmoc-protected compound which was dissolved in 45 ml morpholine in order to cleave the protecting group. After 2 h at RT the excessive morpholine was removed by distillation and the residue was dissolved in 6 ml ice-cold methanol. The insoluble 4-fluorene-9-ylmethyl-morpholine was filtered off and the solution was concentrated.

Yield: 1.23 g (78%) 13

(ii) Synthesis of 14

375 mg (1 mmol) 5 and 127 µl (1 mmol) 4-ethylmorpholine were dissolved in 3 ml dry THF and under argon cooled to −15° C. To this solution 131 µl (1 mmol) chloroformic acid disobutyl ester were added and after 20 min at −15° C. a solution of 351 mg (1 mmol) 13 in 0.5 ml THF was added. After 1 h at −15° C. and 20 h at RT (TLC-control) 64 µl (0.5 mmol) 4-ethylmorpholine and 66 µl (0.5 mmol) chloroformic acid isobutyl ester were added at −15° C. for another activation step. The reaction was terminated after another 2 h by concentrating the reaction batch, dissolving the solid residue in ethylacetate and by processing an ethylacetate phase as described in the context of compound 13.

The obtained raw product was purified chromatographically on silica gel with ethylacetate. Yield: 350 mg (50%) 14.

(iii) Synthesis of XIII 65 mg (0.09 mmol) 14 were dissolved in 9 ml acetonitrile/phosphate buffer (1:1), pH 8.0. Under argon a solution of 25 mg (0.09 mmol) 7 in 9 ml acetonitrile/phosphate buffer were added at RT. The reaction was tracked by means of HPLC and the reaction batch was processed after approx. 3 h after the concentration the solid residue was dissolved in ethylester and the organic phase was subsequently rinsed 3 times with NaCl-solution. It was dried above $Na_2SO_4$, filtrated and concentrated. The raw product was purified chromatographically on silica gel with ethylacetate/petrolether (60:40). The yield was 35 mg (47%) of the corresponding Boc-protected compound. In order to cleave the protecting groups 30 mg of this compound were dissolved in 84 µl (1.1 mmol) trifluoroacetic acid and 840 µl methylenechloride. The reaction was controlled by means of TLC. After completion dry ether was added to the product and the precipitating solid was rinsed with ether several times. Yield: 22.5 mg (70%) XIII.

The following table 4 presents 7 examples of the compounds of the general formula (2) according the invention.

Scheme 17
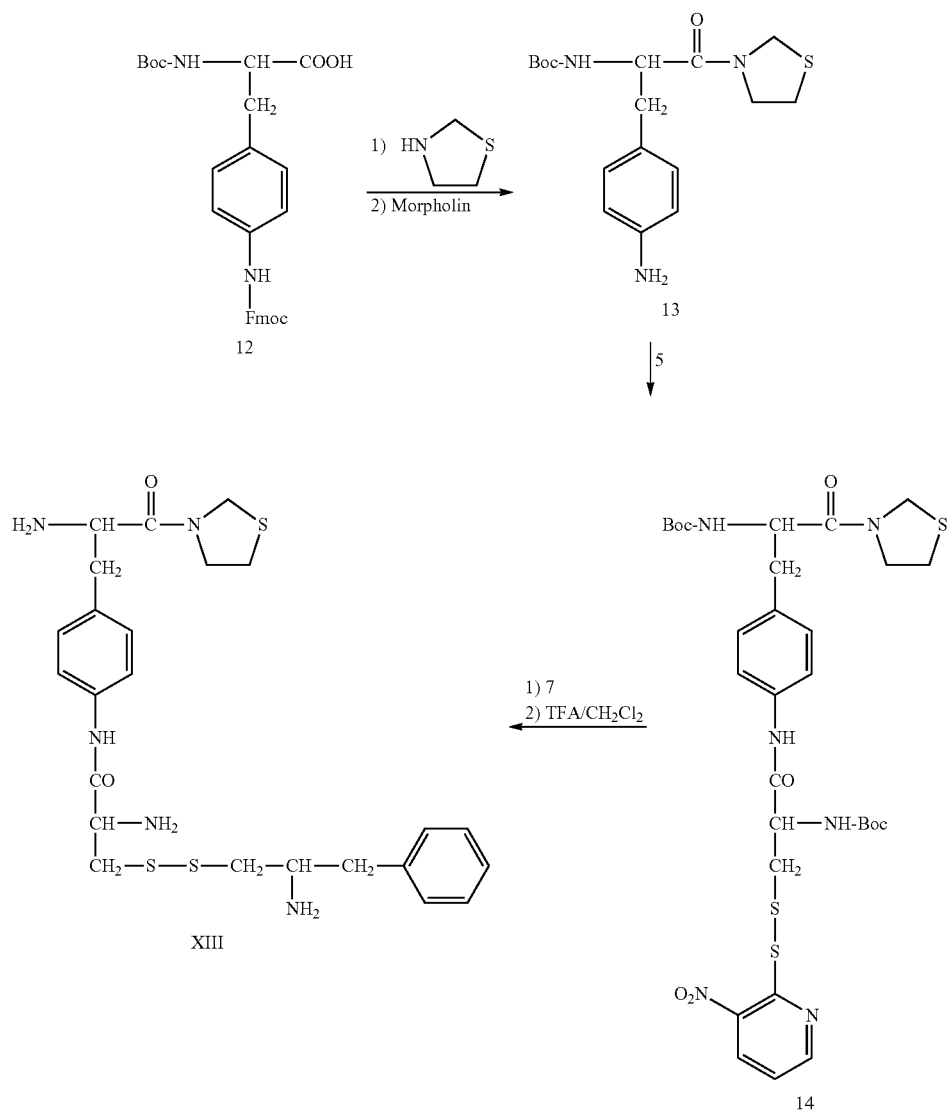
TABLE 4
Examples for compounds of the general formulae A-B-D-E (2)
| No. | B | R⁹ | X | Y | Empirical formula | Molar weight | ESI-MS [m/e] |
|---|---|---|---|---|---|---|---|
| VII | —CH₂— | —CH₂—C₆H₅ | S | H | $C_{15}H_{23}N_3OS_3$ | 357.6 | 358.0 |

TABLE 4-continued
Examples for compounds of the general formulae A-B-D-E (2)
| No. | B | R⁹ | X | Y | Empirical formula | Molar weight | ESI-MS [m/e] |
|-----|---|----|----|----|-------------------|--------------|--------------|
| VIII | 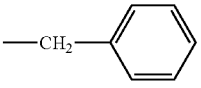 | 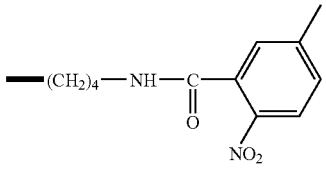 | S | H | $C_{17}H_{27}N_3OS_3$ | 385.6 | 386.0 |
| IX | 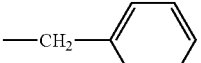 | 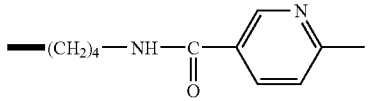 | S | H | $C_{25}H_{33}N_5O_4S_3$ | 563.8 | 564.1 |
| X | 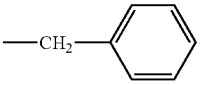 | 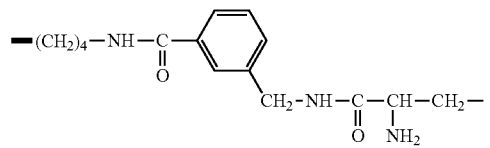 | S | H | $C_{24}H_{33}N_5O_2S_3$ | 519.8 | 520.1 |
| XI | 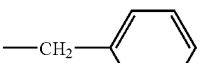 | 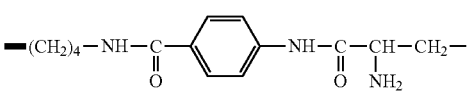 | S | H | $C_{29}H_{42}N_6O_3S_3$ | 618.9 | 619.2 |
| XII | 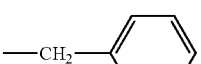 | 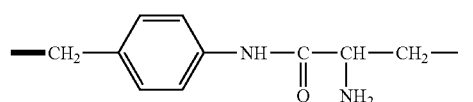 | S | H | $C_{28}H_{40}N_6O_3S_3$ | 604.8 | 605.2 |
| XIII | 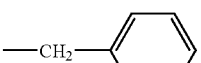 | | S | H | $C_{24}H_{33}N_5O_2S_3$ | 519.8 | 520.2 |

Dual Inhibition of APN and DPIV after Release of the Inhibitors of Prodrugs of the General Formulae (1) and (2)

Eight compounds were selected from the compounds prepared in the afore-mentioned examples 1 and 2 (compounds I and II of the general formulae (1) and (2) and compounds VII, VIII, X, XI, XII and XIII of the general formulae (1) and (2). The mentioned compounds were treated reductively with dithiothreitol (DTT) using the following process to release the inhibitors from the prodrugs.

Process of the Reduction with DTT:

Same volumes of the $7 \cdot 10^{-2}$ M solution of the inhibitor in water or DMF and a 0.35 M aqueous DTT-solution (5 equivalents) were agitated 4 hours at RT.

Subsequently to the reductive treatment of the prodrugs the $IC_{50}$-values were estimated using the following process:

Determination of the $IC_{50}$-Values after Reduction:

Dipeptidyl peptidase IV from pig kidney (EC 3.4.14.5.), lyophilisated powder (Sigma).

Substrate: Ala-Pro-AMC, $[S]=3 \cdot 10^{-5}$ M (2 Km) in the reaction batch.

Buffer: 40 mM Tris/HCl-buffer, pH 7.6, I=0.125 in the reaction batch.

Leucin aminopeptidase, microsomal, from pig kidney (EC 3.4.11.2).

Suspension in 3.5 M $(NH_4)_2SO_4$-solution (Sigma).

Substrate: Leu-AMC, $[S]=1.5 \cdot 10^{-4}$ M (2 Km) in the reaction batch.

Buffer: 40 mM Tris/HCl-buffer, pH 7.2 in the reaction batch.

Procedure:

By dilution with water 10 to 12 solutions with defined inhibitor concentration were prepared from the reduction batch. These were selected from a relevant concentration range, i.e. between complete inhibition and non-influenced enzyme activity.

60 µl of these inhibitor solutions each or water (standard), were incubated with 80 µl of the according diluted enzymes in buffer for 15 minutes at 30° C. and subsequently 60 µl of the according AMC-substrate in water (total volume 200 µl) were added. The release of the 7-Amino-4-methyl-cumarin was traced continuously over a period of 20 minutes at 30° C. using a fluorence-pladt-reader NOVOstar (BMG Labtechnologies). The enzyme concentration was chosen to give a linear increase of the fluorescence during the measuring period.

The excitation- and emission-wavelengths, respectively, were 390 and 460 nm. The measurements were performed in duplicates. The turn-over rates (increase of fluorescence/minutes) were plotted against the concentration of the inhibitor and the $IC_{50}$-values were calculated using the computer program GraFit.

For comparison the $IC_{50}$-values of established inhibitor against DPIV (H-Lys[Z($NO_2$)]-thiazolidide) and APN (actinonine) were estimated.

The results can be derived from table 5.

TABLE 5

Dual inhibition of APN and DP IV after the release (reduction) of the inhibitors from the prodrugs

| Compound | APN (IC 50 [M]) | DP IV (IC 50 [M]) |
| --- | --- | --- |
| I | $1.84 \cdot 10^{-4}$ | $2.25 \cdot 10^{-5}$ |
| II | $1.08 \cdot 10^{-4}$ | $8.07 \cdot 10^{-6}$ |
| VII | $1.66 \cdot 10^{-7}$ | $1.18 \cdot 10^{-5}$ |
| VIII | $1.08 \cdot 10^{-7}$ | $4.51 \cdot 10^{-6}$ |
| X | $1.33 \cdot 10^{-7}$ | $1.25 \cdot 10^{-7}$ |
| XI | $1.90 \cdot 10^{-7}$ | $2.80 \cdot 10^{-7}$ |
| XII | $2.07 \cdot 10^{-7}$ | $2.56 \cdot 10^{-7}$ |
| XIII | $2.40 \cdot 10^{-7}$ | $7.19 \cdot 10^{-6}$ |
| Lys[Z($NO_2$)]-thiazolidide | | $4.34 \cdot 10^{-7}$ |
| Actinonine | $3.02 \cdot 10^{-7}$ | |

Example 3

Inhibition of Phytohaemaglutinine-Induced Proliferation of Mononuclear Cells (MNZ) of Healthy Donors by Compounds V to XIII (Tables 3 and 4)

MNZ were isolated from the peripheral blood of healthy donors by density gradient centrifugation and stimulated in serum-free medium (AIMV) with 1 µg/ml phytohaemaglutinine (PHA). $5 \times 10^4$ MNZ each were incubated in the presence of different inhibitor concentrations (triple measurements) at 37° C. and 5% $CO_2$ in micro test plates for 48 hours. As controls unstimulated cells as well as PHA-stimulated MNZ without inhibitor were cultivated under identical conditions. The proliferation rate of the cells was determined by the incorporation of bromodesoxyuridine in newly synthesized DNA (Biotrak-Assay, GE Healthcare).

The curves shown in FIG. 1 each represent accumulated data (relative values based on PHA-stimulated cells in absence of inhibitor) of at least three different donors.

Example 4

Therapeutic Effect of Compound VII (Table 4) in the Mouse Model of Dextranesulfate-Induced Colitis The therapeutic potential of the substance(s) was/were tested in an established chemical induced model of colitis. In this model an inflammatory reaction is induced in the colon of the animals by dextranesulfate-sodium (DSS) which histological pattern is similar to the human form of chronic inflammatory colon disease (acute push) called colitis ulcerosa. The extent of the inflammatory reaction is dependent on the DSS-concentration. The severity of the illness is measured using an established scoring system in which changes of the stool consistence the detection of blood in faeces as well as the extent of the loss of body weight are being taken into consideration and are valued by scores.

By the application of the inflammatory DSS during the complete duration of the experiments the illness permanently progressed. From a score of 10 a potentially deadly condition of the illness had to be assumed. The maximum reachable therapeutic success was to stop the progression of the inflammatory reaction.

Female Balb/c-mice (8 weeks old) having an average weight of 20 g were fed 3% (w/v) dextranesulfate-sodium with drinking water (ad libitum) during the complete duration of the experiment. After 2 to 3 days colitis-like symptoms (haemorrhagic diarrhoea and loss of body weight) were detectable with all animals. 12 animals each received with day 3 of the experiment daily each 100 µg of substance VII dissolved in physiological salt solution (PBS) or the according amount of solvent (PBS)=placebo-control) by intraperitoneal injection.

Figure 2:
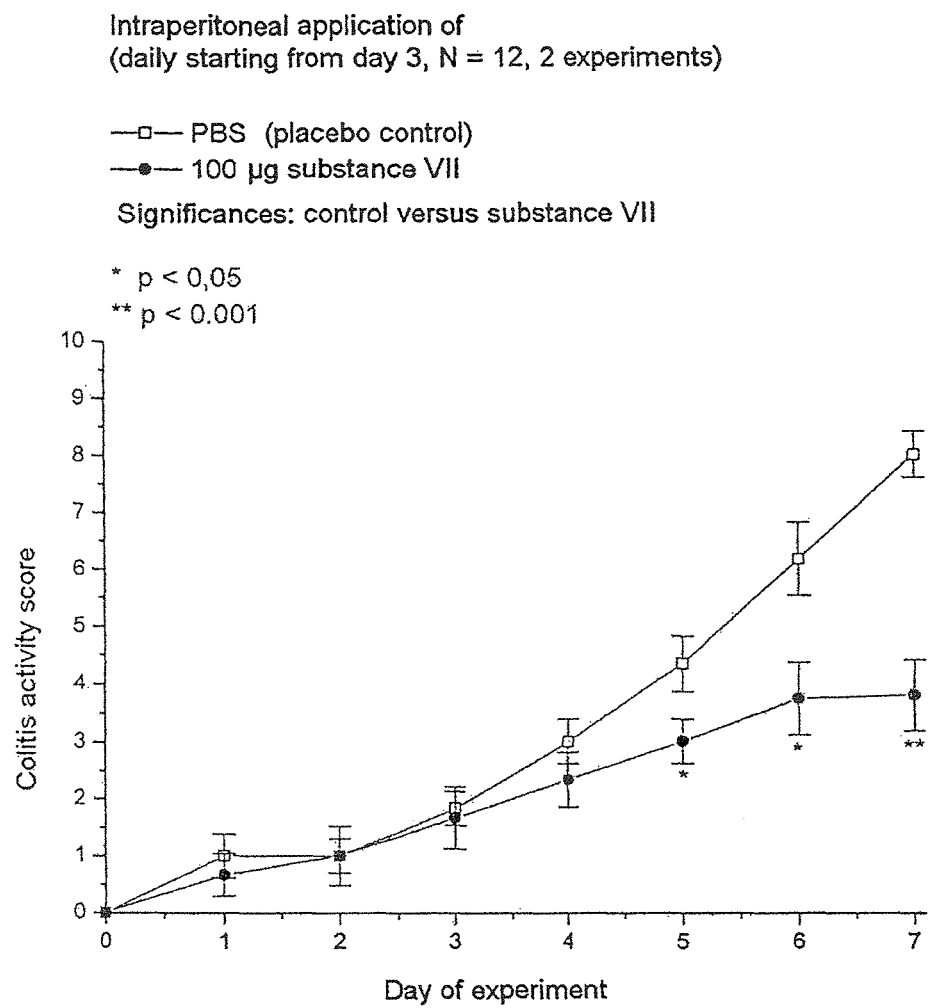
FIG. 2 is a graph showing the therapeutic effect of a substance for colitis activity.

In the graph of FIG. 2 the average severity (score) of those mice treated with substance VII is presented compared to placebo treated animals. The average scores of those mice treated with substance VII was significantly lower on days 5 to 7 of the experiment as those of the placebo treated animals. At the end of the experiment those animals treated with substance VII reached on average approximately half the score of the control animals.

Example 5

Figure 3:
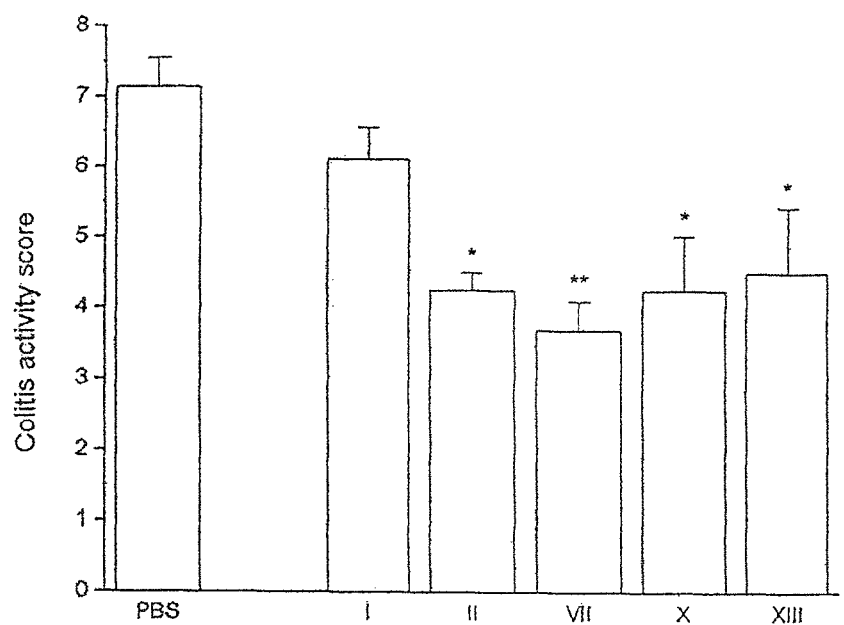
FIG. 3 is a graph showing the therapeutic effect of a substance for colitis activity.
Figure 4:
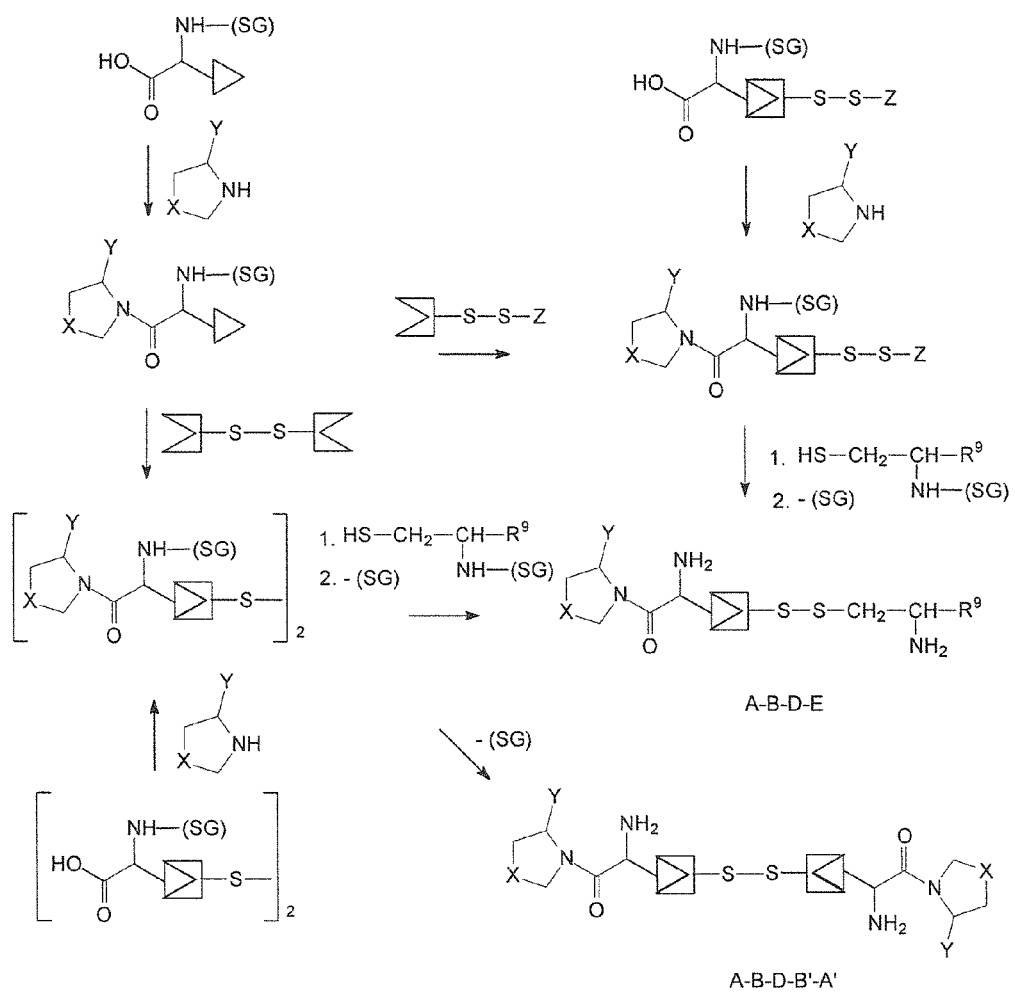
FIG. 4 sets forth the synthetic scheme of synthesis 1 for compounds A-B-D-B'-A' and A-B-D-E.

Therapeutic Success of Several Compounds of the General Formulae (1) and (2) Given in Table 3 and 4 in the Mouse Model of DSS-Induced Colitis In FIG. 3 the therapeutic potential of various exemplary substances on day 7 of the experiment (end of experiment) is shown for the mouse model of DSS-induced colitis. The colitis activity score was determined according to the method described in example 4.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:
1. Compounds of the general formulae (1) or (2)

$$A\text{-}B\text{-}D\text{-}B'\text{-}A' \quad (1)$$

or $$A\text{-}B\text{-}D\text{-}E \quad (2),$$

wherein

A and A' may be identical or different and are the residue

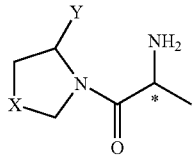

wherein X is selected from the group consisting of S, O, $CH_2$, $CH_2CH_2$, $CH_2O$ and $CH_2NH$, and Y is selected from the group consisting of H and CN, and * designates a chiral carbon atom in the S-, or L-configuration;

B and B' may be identical or different and are residues selected from the group consisting of optionally containing O, S or N unsubstituted or substituted, unbranched or branched alkylene residue, cycloalkylene residue, aralkylene residue, heterocycloalkylene residue, heteroarylalkylene residue, arylamidoalkylene residue, heteroarylamidoalkylene residue, unsubstituted or mono- or poly-substituted arylene residue and heteroarylene residue having one or more five-, six- or seven-membered ring(s);

D is selected from the group consisting of —S—S— and —Se—Se—; and

E is selected from the group consisting of —$CH_2$—CH($NH_2$)—$R^9$ and —$CH_2$—*CH($NH_2$)—$R^9$, respectively wherein $R^9$ is a residue selected from the group consisting of optionally containing O, N or S unsubstituted or substituted, unbranched or branched alkyl residue, cycloalkyl residue, aralkyl residue, heterocycloalkyl residue, heteroarylalkyl residue, arylamidoalkyl residue, heteroarylamidoalkyl residue, unsubstituted or mono- or polysubstituted aryl residue or heteroaryl residue having one or more five-, six- or seven-membered ring(s) and * designates a chiral carbon atom in the S-, or L-configuration;

or the acid addition salts thereof with organic and/or inorganic acids.

2. Compounds of the general formulae (1) or (2) according to claim 1, wherein B and/or B' is
(a) a residue $R^1$, which is a straight-chained or branched alkylene residue having 1 to 6 carbon atoms which is selected from the group consisting of —$CH_2$—, —$CH_2$—$CH_2$— and $(H_3C)_2$—C<; or
(b) a residue —$(CH_2)_n$—$R^2$—$R^3$—$R^4$—, wherein n is an integer from 1 to 5; $R^2$ is selected from the group consisting of —NH— and —(NH)—C(=NH)—NH—, if $R^3$ is O=C< or —$SO_2$— or wherein $R^2$ is O=C< if $R^3$ is —NH—; $R^4$ is a residue selected from the group consisting of optionally containing O, N or S unsubstituted or substituted unbranched or branched alkylene-residue, cycloalkylene-residue, aralkylene-residue, heterocycloalkylene-residue, heteroarylalkylene-residue, unsubstituted or mono-substituted or poly-substituted arylene-residue and heteroarylene-residue with one or more five-, six- or seven-membered ring(s); or
(c) is a residue —$R^7$—$R^8$—, wherein $R^7$ is a mono- or poly substituted benzylene residue and $R^8$ is a single bond or a residue selected from the group consisting of optionally containing O, N or S unsubstituted or substituted, unbranched or branched alkylene residue, cycloalkylene residue, aralkylene residue, heterocycloalkylene residue or heteroarylalkylene residue, which might contain as functional groups preferably one or more amino groups, carbonyl groups or carboxyl groups or an unsubstituted or mono- or poly-substituted arylene residue or heteroarylene residue with one or more than one five-, six-, or seven-membered ring(s).

3. Compounds of the general formulae (1) or (2) according to claim 1, wherein B is a residue —$(CH_2)_n$—$R^2$—$R^3$—$R^4$ wherein $R^4$ is —CH(COOH)—$R^1$—, wherein $R^1$ has the afore-mentioned meaning if $R^2$ is O=C< and $R^3$ is —NH—; or

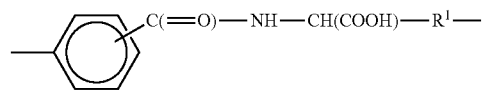

(substitution at position 2, 3 or 4)
wherein $R^1$ has the afore-mentioned meaning if $R^2$ is O=C< and $R^3$ is —NH—; or
—CH(NH$R^5$)—$R^1$— if $R^2$ is —NH— or —NH—C(=NH)—NH— and $R^3$ is O=C< wherein $R^5$ is H or a residue selected from the group consisting of an acyl residue, a fluorene-9-ylmethoxycarbonyl residue, a tert-butyloxycarbonyl residue and a benzoyl residue; or

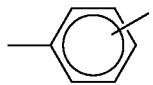

(substitution at position 2, 3 or 4), wherein $R^4$ is phenylene and $R^2$ is —NH— or —NH—C(=NH)—NH— if $R^3$ is O=C< or —SO$_2$— or wherein $R^2$ is O=C< if $R^3$ is —NH—; or

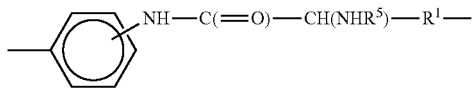

(substitution at position 2, 3 or 4)
wherein $R^5$ is H or a residue selected from the group consisting of an acyl residue, a fluoren-9-ylmethoxycarbonyl residue or a benzoyl residue and $R^2$ is —NH— or —NH—C(=NH)—NH— if $R^3$ is O=C< or —SO$_2$— or wherein $R^2$ is O=C< if $R^3$ is —NH—; or

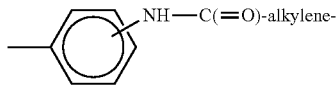

(substitution at position 2, 3 or 4),
wherein alkylene is an unbranched or branched alkylene residue having 1 to 6 carbon atoms and $R^2$ is —NH— or —NH—C(=NH)—NH— if $R^3$ is O=C< or —SO$_2$— or wherein $R^2$ is O=C< if $R^3$ is —NH—; or

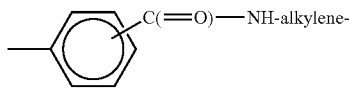

(substitution at position 2, 3 or 4),
wherein alkylene is an unbranched or branched alkylene residue having 1 to 6 carbon atoms and $R^2$ is —NH— or —NH—C(=NH)—NH— if $R^3$ is O=C< or —SO$_2$— or wherein $R^2$ is O=C< if $R^3$ is —NH—; or

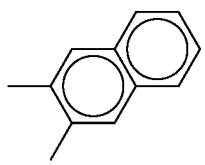

wherein $R^2$ is —NH— or —NH—C(NH)—NH— if $R^3$ is O=C< or —SO$_2$— or wherein $R^2$ is O=C< if $R^3$ is —NH—; or

(substitution position 2, 3 or 4)
(substitution at the ring depending on the position of $R^6$)
wherein $R^6$ is selected from the group consisting of H, NO$_2$, CN, halogen and an acyl residue and $R^2$ is —NH— or —NH—C(=NH)—NH— if $R^3$ is O=C< or —SO$_2$— or wherein $R^2$ is O=C< if $R^3$ is —NH—; or

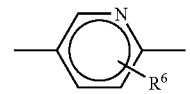

(substitution at position 3, 4 or 6), wherein $R^6$ is selected from the group consisting of H, NO$_2$, CN, halogen and an acyl residue and $R^2$ is —NH— or —NH—C(=NH)—NH— if $R^3$ is O=C< or —SO$_2$— or wherein $R^2$ is O=C< if $R^3$ is —NH—; or

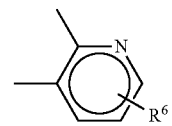

(substitution at position 4, 5 or 6), wherein $R^6$ is selected from the group consisting of H, NO$_2$, CN, halogen and an acyl residue and $R^2$ is —NH— or —NH—C(=NH)—NH— if $R^3$ is O=C< or —SO$_2$— or wherein $R^2$ is O=C< if $R^3$ is —NH; or

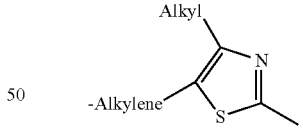

wherein and $R^2$ is —NH— or —NH—C(=NH)—NH— if $R^3$ is O=C< or —SO$_2$— or
wherein $R^2$ is O=C< if $R^3$ is —NH—.

4. Compounds of the general formulae (1) or (2) according to claim 1, wherein B is a residue —$R^7$—$R^8$— wherein $R^7$ and $R^8$ in combination are a residue

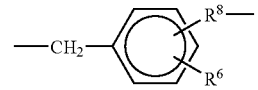

(position of R⁶ is dependent of the position R⁸) wherein R⁸ is a single bond or a residue selected from the group consisting of optionally containing O, N or S unsubstituted or substituted, unbranched or branched alkylene residue, cycloalkylene residue, aralkylene residue, heterocycloalkylene residue or heteroarylalkylene residue, which might contain as functional groups preferably one or more amino groups, carbonyl groups or carboxyl groups or an unsubstituted or mono- or poly-substituted arylene residue or heteroarylene residue with one or more than one five-, six-, or seven-membered ring(s) and R⁶ is selected from the group consisting of H, NO₂, CN, halogen and an acyl residue.

5. Compounds of the formulae (1) or (2) according to claim 1, wherein B is a residue —R⁷—R⁸— wherein R⁷ is a mono- or poly-substituted benzylene residue and R⁸ is NH— or —C₁- to C₆-alkylene —NH— in combination with
 —C(=O)—C₁- to C₆-alkylene- or
 —C(=O)-arylene- or
 —SO₂—C₁- to C₆-alkylene- or
 —SO₂-arylene- or

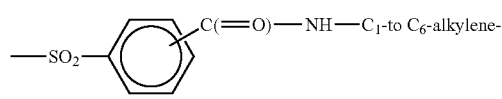

(substitution at position 2, 3 or 4) or
 —C(=O)—CH(NHR⁵)—R¹ wherein R¹ and R⁵ have the afore-mentioned meanings; or
O=C< in combination with
 —NH—C₁- to C₆-alkylene- or
 —NH-arylene- or
 —NH—CH(COOH)—R¹— wherein R¹ has the afore-mentioned meanings; or
 —O—C₁- to C₆-alkylene- or
 —O-arylene- or
 —O-alkylene-NH—C(=O)—CH(NH₂)—R¹— wherein R¹ has the afore-mentioned meanings, or
 —O—C₁- to C₆-alkylene-C(=O)—NH—CH(COOH)—R¹—, wherein R¹ has the afore-mentioned meanings.

6. Compounds of the general formulae (1) or (2) according to claim 1, wherein the acid addition salts are salts of pharmaceutically acceptable acids.

7. Compounds of the general formula (1) according to claim 1, namely compounds of the general formula (1a)

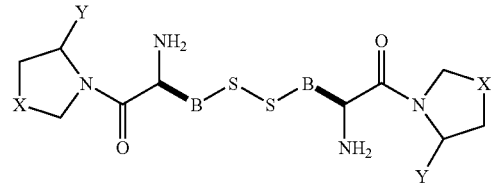

(1a)

wherein X, Y and B are as defined in claim 1 or the acid additions salts thereof.

8. Compounds of the general formula (1a) according to claim 7, wherein X, Y and B have the following meanings

| No. | B | X | Y | Empirical formula |
|---|---|---|---|---|
| I | —CH₂— | —CH₂— | H | C₁₄H₂₆N₄O₂S₂ |
| II | —CH₂— | S | H | C₁₂H₂₂N₄O₂S₄ |
| III | —CH₂— | —CH₂— | CN | C₁₆H₂₄N₆O₂S₂ |
| IV | —(CH₂)₄—NH—C(=O)—CH(NH₂)—CH₂— | S | H | C₂₄H₄₆N₈O₄S₄ |
| V | —(CH₂)₄—NH—C(=O)—(4-methyl-2-nitrophenyl) | S | H | C₃₂H₄₂N₈O₈S₄ |
| VI | —(CH₂)₄—NH—C(=O)—(methylpyridyl) | S | H | C₃₀H₄₂N₈O₄S₄ | or the acid addition salts thereof.

9. Compounds of the general formula (2) according to claim 1, namely compounds of the general formula (2a)

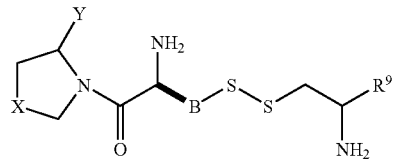
(2a)

wherein X, Y, $R^9$ and B are as defined in claim 1 or the acid addition salts thereof.

10. Compounds of the general formula (2a) according to claim 9, wherein X, Y, $R^9$ and B have the following meanings:

| No. | B | $R^9$ | X | Y | Empirical formula |
|---|---|---|---|---|---|
| VII | —CH$_2$— | —CH$_2$—C$_6$H$_5$ | S | H | $C_{15}H_{23}N_3OS_3$ |
| VIII | —C(CH$_3$)$_2$— | —CH$_2$—C$_6$H$_5$ | S | H | $C_{17}H_{27}N_3OS_3$ |
| IX | —(CH$_2$)$_4$—NH—C(=O)—(4-methyl-2-nitrophenyl) | —CH$_2$—C$_6$H$_5$ | S | H | $C_{25}H_{33}N_5O_4S_3$ |
| X | —(CH$_2$)$_4$—NH—C(=O)—(6-methylpyridin-3-yl) | —CH$_2$—C$_6$H$_5$ | S | H | $C_{24}H_{33}N_5O_2S_3$ |
| XI | —(CH$_2$)$_4$—NH—C(=O)—C$_6$H$_4$—CH$_2$—NH—C(=O)—CH(NH$_2$)—CH$_2$— | —CH$_2$—C$_6$H$_5$ | S | H | $C_{29}H_{42}N_6O_3S_3$ |
| XII | —(CH$_2$)$_4$—NH—C(=O)—C$_6$H$_4$—NH—C(=O)—CH(NH$_2$)—CH$_2$— | —CH$_2$—C$_6$H$_5$ | S | H | $C_{28}H_{40}N_6O_3S_3$ |
| XIII | —CH$_2$—C$_6$H$_4$—NH—C(=O)—CH(NH$_2$)—CH$_2$— | —CH$_2$—C$_6$H$_5$ | S | H | $C_{24}H_{33}N_5O_2S_3$ | or the acid addition salts thereof.

11. A process for preparing compounds of the general formulae (1) or (2)

A-B-D-B'-A'  (1) or

A-B-D-E  (2) wherein

A, B, D and E are as defined in claim 1, wherein according to scheme of synthesis 1
compounds of the general formula

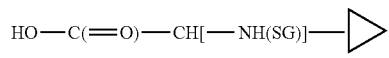

wherein (SG) is a protecting group and

is a structure element of B are transformed with a heterocyclic compound of the general formula

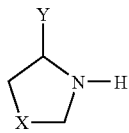

wherein X is selected from the group consisting of S, O, $CH_2$, $CH_2CH_2$, $CH_2O$ and $CH_2NH$ and Y is selected from the group consisting of H and CN; the obtained condensation product of the formula

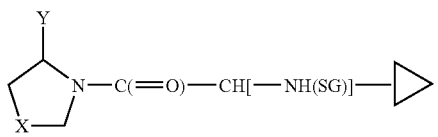

is transformed with a compound of the general formula

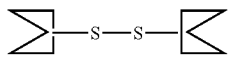

wherein

is a structure element of B; and the resulting reaction product is transformed being cleaved from the protecting group (SG) into a compound of the general formula A-B-D-B'-A' (1) wherein A and A' may be identical or different and B and B' may be identical or different and wherein A, A', B, B' and D may have the afore-mentioned meanings; or
compounds of the general formula

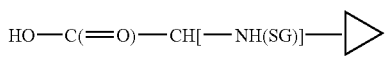

wherein (SG) is a protecting group and

is a structure element of B are transformed with a heterocyclic compound of the general formula

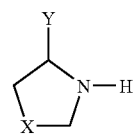

wherein X is selected from the group consisting of S, O, $CH_2$, $CH_2CH_2$, $CH_2O$ and $CH_2NH$ and Y is selected from the group consisting of H CN; the resulting condensation product of the formula

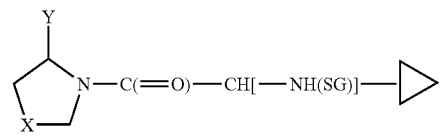

is transformed with a compound of the general formula

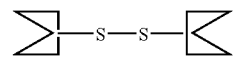

wherein

is a structure element of B; and the resulting reaction product is transformed with a compound of the general formula

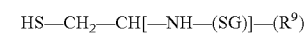

and is transformed being cleaved from the protecting groups (SG) into a compound of the general formula A-B-D-E (2), wherein A, B, D and E may have the afore-mentioned meanings; or
compounds of the general formula

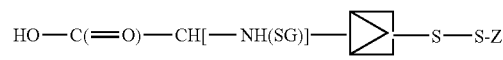

wherein (SG) is a protecting group,

is a structure element of B and Z is a residue, which activates an —S—S-group for a thiol exchange, is transformed with a heterocyclic compound of the general formula

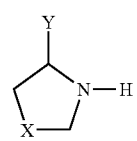

wherein X is selected from the group consisting of S, O, CH$_2$, CH$_2$CH$_2$, CH$_2$O and CH$_2$NH and Y is selected from the group consisting of H and CN; the obtained condensation product of the formula

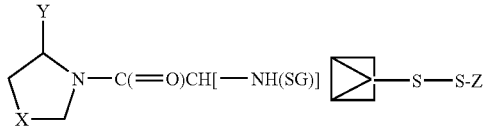

is transformed with a compound of the general formula

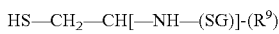

and is transformed being cleaved from the protecting groups (SG) into a compound of the general formula A-B-D-E (2), wherein A, B, D and E may have the afore-mentioned meanings; or compounds of the general formula

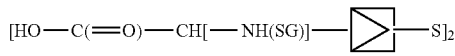

wherein SG is a protecting group and

is a structure element of B is transformed with a heterocyclic compound of the general formula

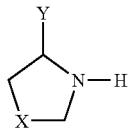

wherein X is selected from the group consisting of S, O, CH$_2$, CH$_2$CH$_2$, CH$_2$O and CH$_2$NH and Y is selected from the group consisting of H and CN; and the obtained reaction product is transformed with a compound of the general formula

HS—CH$_2$—CH[—NH—(SG)]-R$^9$ into a compound of the general formula A-B-D-E (2) wherein A, B, D and E may have the afore-mentioned meanings; or compounds of the general formula

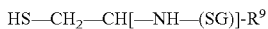

wherein SG is a protecting group and

is a structure element of B, is transformed with a heterocyclic compound of the general formula

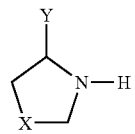

wherein X is selected from the group consisting of S, O, CH$_2$, CH$_2$CH$_2$, CH$_2$O and CH$_2$NH and Y is selected from the group consisting of H and CN; and the obtained reaction product is transformed being cleaved from the protecting groups SG into a compound of the general formula A-B-D-B'-A' (1) wherein A and A' may be identical or different and B and B' may be identical or different and wherein A, A', B, B' and D may have the afore-mentioned meanings; or compounds of the general formula

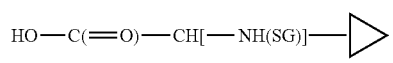

wherein (SG) is a protecting group and

is a structure element of B are transformed with a heterocyclic compound of the general formula

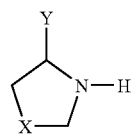

wherein X is selected from the group consisting of S, O, CH$_2$, CH$_2$CH$_2$, CH$_2$O and CH$_2$NH and Y is selected from the group consisting of H and CN; the obtained condensation product of the formula

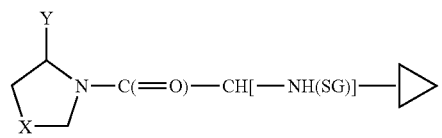

is transformed with a compound of the general formula

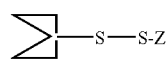

wherein

is a structure element of B and Z is a residue which activates an —S—S-group for a thiol exchange and (SG) is a protecting group; and the obtained reaction product of the formula

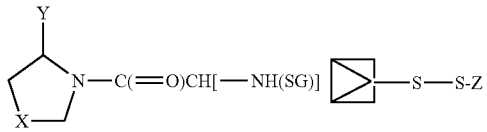

is transformed with a compound of the general formula

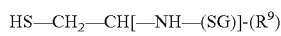

HS—CH$_2$—CH[—NH—(SG)]-(R$^9$)

and is transformed being cleaved from the protecting group (SG) into a compound of the general formula A-B-D-E (2) wherein A, B, D and E may have the afore-mentioned meanings.

12. The compounds according to claim 1, wherein said compounds are inhibitors of at least one selected from the group consisting of inhibitor of dipeptidyl peptidase IV (DPIV), inhibitor of peptidases with dipeptidyl peptidase IV analogous enzymatic effect, inhibitor of alanyl aminopeptidase N (APN) and inhibitor of peptidases with alanyl aminopeptidase N analogous enzymatic effect.

13. The compounds according to claim 1, wherein said compounds are precursors or prodrugs for inhibitors of at least one selected from the group consisting of inhibitor of dipeptidyl peptidase IV (DPIV), inhibitor of peptidases with dipeptidyl peptidase IV analogous enzymatic effect, inhibitor of alanyl aminopeptidase N (APN) and inhibitor of peptidases with alanyl aminopeptidase N analogous enzymatic effect.

14. A method for treating type II diabetes and related diseases selected from the group consisting of arteriosclerosis, colitis and psoriasis, said method comprising the step of administering to a patient in need thereof at least one compound of the general formulae (1) or (2)

A-B-D-B'-A'    (1) and

A-B-D-E    (2), wherein

A and A' may be identical or different and are the residue

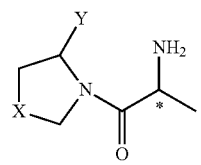

wherein X is selected from the group consisting of S, O, CH$_2$, CH$_2$CH$_2$, CH$_2$O and CH$_2$NH, and Y is selected from the group consisting of H and CN, and * designates a chiral carbon atom in the S—, or L-configuration;

B and B' may be identical or different and are residues selected from the group consisting of optionally containing O, S or N unsubstituted or substituted, unbranched or branched alkylene residue, cycloalkylene residue, aralkylene residue, heterocycloalkylene residue, heteroarylalkylene residue, arylamidoalkylene residue, heteroarylamidoalkylene residue, unsubstituted or mono- or poly-substituted arylene residue and heteroarylene residue having one or more five-, six- or seven-membered ring(s);

D is selected from the group consisting of —S—S— and —Se—Se—; and

E is selected from the group consisting of —CH$_2$—CH(NH$_2$)—R$^9$ and —CH$_2$—*CH(NH$_2$)—R$^9$, respectively wherein R$^9$ is a residue selected from the group consisting of optionally containing O, N or S unsubstituted or substituted, unbranched or branched alkyl residue, cycloalkyl residue, aralkyl residue, heterocycloalkyl residue, heteroarylalkyl residue, arylamidoalkyl residue, heteroarylamidoalkyl residue, unsubstituted or mono- or polysubstituted aryl residue or heteroaryl residue having one or more five-, six- or seven-membered ring(s) and * designates a chiral carbon atom in the S—, or L-configuration;

or the acid addition salts thereof with organic and/or inorganic acids.

15. A method for preparing a medicament or a cosmetic preparation, said method comprising the step of combining a pharmaceutical carrier with a compound of the general formulae (1) or (2)

A-B-D-B'-A'    (1) or

A-B-D-E    (2), wherein

A and A' may be identical or different and are the residue

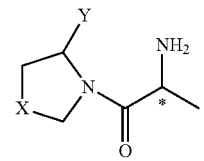

wherein X is selected from the group consisting of S, O, CH$_2$, CH$_2$CH$_2$, CH$_2$O and CH$_2$NH, and Y is selected from the group consisting of H and CN, and * designates a chiral carbon atom in the S—, or L-configuration;

B and B' may be identical or different and are residues selected from the group consisting of optionally containing O, S or N unsubstituted or substituted, unbranched or branched alkylene residue, cycloalkylene residue, aralkylene residue, heterocycloalkylene residue, heteroarylalkylene residue, arylamidoalkylene residue, heteroarylamidoalkylene residue, unsubstituted or mono- or poly-substituted arylene residue and heteroarylene residue having one or more five-, six- or seven-membered ring(s);

D is selected from the group consisting of —S—S— and —Se—Se—; and

E is selected from the group consisting of —CH$_2$—CH(NH$_2$)—R$^9$ and —CH$_2$—*CH(NH$_2$)—R$^9$, respectively wherein R$^9$ is a residue selected from the group consisting of optionally containing O, N or S unsubstituted or substituted, unbranched or branched alkyl residue, cycloalkyl residue, aralkyl residue, heterocycloalkyl residue, heteroarylalkyl residue, arylamidoalkyl residue, heteroarylamidoalkyl residue, unsubstituted or mono- or polysubstituted aryl residue or heteroaryl residue having one or more five-, six- or seven-membered ring(s) and * designates a chiral carbon atom in the S-, or L-configuration;

or the acid addition salts thereof with organic and/or inorganic acids.

16. The method according to claim 14, further comprising the step of generating at least one inhibitor selected from the group consisting of inhibitor of dipeptidyl peptidase IV (DPIV), inhibitor of peptidases with dipeptidyl peptidase IV analogous enzymatic effect, inhibitor of alanyl aminopeptidase N (APN) and inhibitor of peptidases with alanyl aminopeptidase N analogous enzymatic effect, from at least one of the compounds of the general formulae (1) or (2).

17. The method according to claim 16, comprising the step of applying said method under reducing physiological or pathophysiological conditions.

18. A process for generating at least one inhibitor selected from the group consisting of inhibitor of dipeptidyl peptidase IV (DPIV), inhibitor of peptidases with dipeptidyl peptidase IV analogous enzymatic effect, inhibitor of alanyl aminopeptidase N (APN) and inhibitor of peptidases with alanyl aminopeptidase N analogous enzymatic effect, from at least one of the compounds of the general formulae (1) or (2) according to claim 1, comprising the step of exposing at least one compound of the general formulae (1) or (2) to reducing conditions.

19. The process according to claim 18, comprising the step of exposing at least one compound of the general formulae (1) or (2) to reducing physiological conditions in vivo.

20. A pharmaceutical preparation comprising at least one of the compounds of the general formulae (1) or (2) according to claim 1, optionally in combination with at least one selected from the group consisting of pharmaceutically acceptable carrier(s), auxiliary substance(s) and adjuvant(s).

21. A cosmetic preparation comprising at least one compound of at least one of the general formulae (1) or (2) according to claim 1, optionally in combination with at least one selected from the group consisting of pharmaceutically acceptable carrier(s), auxiliary substance(s) and adjuvant(s).

22. Compounds according to claim 3, wherein $R^5$ is a benzyloxycarbonyl residue.

23. Compounds of the general formulae (1) or (2) according to claim 6, wherein said acid addition salts are selected from the group consisting of hydrochlorides, trifluoracetates, tartrates, succinates, formiates and citrates.

24. Compounds of the general formula (1) according to claim 7, wherein the acid addition salts are acid additions salts with pharmaceutically acceptable inorganic and/or organic acids.

25. Compounds of the general formula (1a) according to claim 8, wherein the acid addition salts are acid addition salts with pharmaceutically acceptable inorganic and/or organic acids.

26. Compounds of the general formula (2) according to claim 9, wherein the acid addition salts are acid addition salts with pharmaceutically acceptable inorganic and/or organic acids.

27. Compounds of the general formula (2a) according to claim 10, wherein said acid addition salts are acid addition salts with pharmaceutically acceptable inorganic and/or organic acids.

28. The method according to claim 15, further comprising the step of generating at least one inhibitor selected from the group consisting of inhibitor of dipeptidyl peptidase IV (DPIV), inhibitor of peptidases with dipeptidyl peptidase IV analogous enzymatic effect, inhibitor of alanyl aminopeptidase N (APN) and inhibitor of peptidases with alanyl aminopeptidase N analogous enzymatic effect, from at least one of the compounds of the general formulae (1) or (2).

29. The method according to claim 28, wherein said method comprises the step of applying the method under reducing conditions, wherein said conditions are under which —S—S-bonds or —Se—Se-bonds are transformed into —SH-groups or SeH-groups.

* * * * *